(12) United States Patent
Takenaka et al.

(10) Patent No.: US 7,754,903 B2
(45) Date of Patent: Jul. 13, 2010

(54) CURABLE POLYCYCLIC COMPOUNDS AND PROCESS FOR THE PRODUCTION THEREOF

(75) Inventors: Junji Takenaka, Yamaguchi (JP); Hiromasa Yamamoto, Yamaguchi (JP); Kenji Tanaka, Yamaguchi (JP)

(73) Assignee: Tokuyama Corporation, Mikage-Cho, Shunan-Shi, Yamaguchi (JP)

( * ) Notice: Subject to any disclaimer, the term of this patent is extended or adjusted under 35 U.S.C. 154(b) by 1153 days.

(21) Appl. No.: 10/560,794

(22) PCT Filed: Jun. 18, 2004

(86) PCT No.: PCT/JP2004/008959

§ 371 (c)(1),
(2), (4) Date: Dec. 15, 2005

(87) PCT Pub. No.: WO2004/113313

PCT Pub. Date: Dec. 29, 2004

(65) Prior Publication Data

US 2006/0252911 A1 Nov. 9, 2006

(30) Foreign Application Priority Data

| Jun. 20, 2003 | (JP) | ............... | 2003-175754 |
| Sep. 17, 2003 | (JP) | ............... | 2003-324162 |
| Sep. 17, 2003 | (JP) | ............... | 2003-324268 |
| Oct. 17, 2003 | (JP) | ............... | 2003-358270 |
| Oct. 20, 2003 | (JP) | ............... | 2003-359205 |

(51) Int. Cl.
*C07D 493/00* (2006.01)
*C07D 303/00* (2006.01)

(52) U.S. Cl. ............... 549/510; 549/512; 549/513

(58) Field of Classification Search ............... 549/510, 549/512, 513
See application file for complete search history.

(56) References Cited

U.S. PATENT DOCUMENTS

| 3,297,724 A | 1/1967 | McMonnell | |
| 3,404,102 A | 10/1968 | Starcher | |
| 6,235,851 B1 * | 5/2001 | Ishii et al. | ............... 525/127 |

FOREIGN PATENT DOCUMENTS

| CN | 456949 | 7/1968 |
| GB | 982151 | 2/1965 |
| JP | 48-66696 | 9/1973 |
| JP | 60-100537 | 6/1985 |
| JP | 60-124608 | 7/1985 |
| JP | 63-307844 | 12/1988 |
| JP | 2-104553 | 4/1990 |
| JP | 2-196744 | 8/1990 |
| JP | 3-118342 | 5/1991 |
| JP | 8-38909 | 2/1996 |
| JP | 9-327626 | 12/1997 |
| JP | 10-286467 | 10/1998 |
| JP | 2000-219646 | 8/2000 |
| JP | 2000-302774 | 10/2000 |
| JP | 2000-327950 | 11/2000 |
| JP | 2000-327994 | 11/2000 |
| JP | 2001-26563 | 1/2001 |
| JP | 2001-81286 | 3/2001 |
| JP | 2003-73452 | 3/2003 |
| JP | 2003-261648 | 9/2003 |
| JP | 2003-321530 | 11/2003 |
| JP | 2003-327951 | 11/2003 |
| JP | 2004-83732 | 3/2004 |
| JP | 2004-250434 | 9/2004 |

OTHER PUBLICATIONS

Dearborn et al DN 48:13253 (1953) abstract.*
Ciba DN 57:75868 (1962) abstract.*

(Continued)

*Primary Examiner*—Janet L. Andres
*Assistant Examiner*—Raymond Covington
(74) *Attorney, Agent, or Firm*—Norris, McLaughlin & Marcus

(57) ABSTRACT

The present invention discloses a curable polycyclic compound represented by the following formula (1):

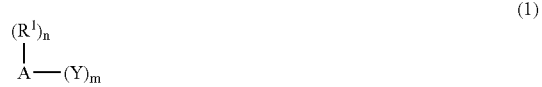

(1)

{wherein A is a di- to hexa-valent group derived from a polycyclic hydrocarbon compound; $R^1$ is an alkyl group of 1 to 4 carbon atoms, a perfluoroalkyl group of 1 to 4 carbon atoms, or a fluorine atom; n is an integer of 0 to 2; m is an integer of 2 to 4; and Y is a group represented by the following formula (2) or (3):

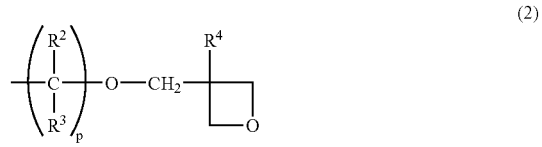

(2)

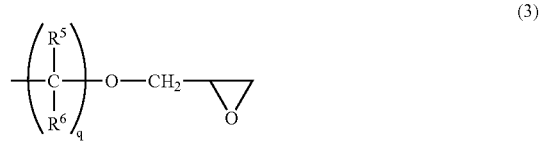

(3)

(wherein $R^2$, $R^3$, $R^5$ and $R^6$ are each independently a hydrogen atom, a fluorine atom or an alkyl group of 1 to 4 carbon atoms; $R^4$ is a methyl group or an ethyl group; and p and q are each independently an integer of 0 to 4)}.

7 Claims, No Drawings

OTHER PUBLICATIONS

Shiryaev, et al.; "The Effect of Solvent Polarity on the Conformational Equilibrium in Glycidyl and Thioglycidyl Esthers and Esters"; V.V. Kuibyshev Samarsk Polytechnical Institute; vol. 27, No. 6, Jun. 1991, pp. 1249-1253.

Butenko, et al.; "Synthesis of 2,2-(Adamantylene-1,3)-Diethanoic Acids"; The Volgograd Polytehnical Institute; A.V. Topchiev Institute of Petrochemical Synthesis, Russian Academy of Sciences, Moscow, 117912; pp. 1612-1615.

Aigami, et al.; "Biologically Active Polycycloalkanes. 1. Antiviral Adamantane Derivaties"; Polycycloalkanes; Journal of Medicinal Chemistry; 1975, vol. 18, No. 7, pp. 713-721.

Twardowski, et al.; "The Effect of Chain Stiffness in Lightly Crosslinked Epoxides"; J.M.S.—Pur Appl. Chem., 1993, A30(1), pp. 75-89.

Smyth, et al.; Range Finding Toxicity Data VII; American Industrial Hygiene Association Journal, 1969, 30(5), pp. 470-476.

* cited by examiner

CURABLE POLYCYCLIC COMPOUNDS AND PROCESS FOR THE PRODUCTION THEREOF

TECHNICAL FIELD

The present invention relates to novel curable polycyclic compounds useful as a raw material for encapsulant, adhesive, etc.; a process for production thereof; a curable composition prepared using the compound; an encapsulant for light-emitting diode, comprising the curable composition; and a light-emitting diode encapsulated with the encapsulant. The curable polycyclic compounds have oxetanyl group or epoxy group as a functional group capable of giving rise to a curing reaction.

BACKGROUND ART

Polycyclic hydrocarbon compounds show non-aromaticity, have a stiff molecule, have a unique structure and accordingly are drawing attention in various fields. There are known, for example, diallyl adamantanedicarboxylate (JP 1988-100537 A) and adamantanedi(meth)acrylate derivatives (JP 1985-307844 A), each as a monomer for plastic lens superior in optical properties and heat resistance.

There are also known particular adamantane compounds having (meth)acryl group (JP 2000-327950 A and JP 2000-327994 A), as a monomer for coating composition superior in adhesivity, light resistance, chemical resistance and hardness or as a monomer for coating.

Meanwhile, in recent years, there has been a remarkable progress with respect to the light-emitting diode (hereinafter, abbreviated as LED) which is a semiconductor light-emitting device produced with a compound semiconductor. As the light-emitting material therefor, there were developed aluminum•indium•gallium•phosphorus (AlInGaP) for red to bitter orange color light and gallium nitride (GaN) for blue color light. There was also realized a near-ultraviolet LED of 400 nm or shorter (e.g. 365 nm or 370 nm).

There was also achieved a white LED by, for example, combining a fluorescent material with a blue LED or a near-ultraviolet LED.

LED has various advantages such as long life, high thermal stability, easy light control, low operating voltage and the like. Owing to the high evaluation of LED particularly for the high light-emitting efficiency and high reliability, active application of LED is being pushed forward in the fields such as display, display panel, vehicle lighting, signal lamp, mobile telephone, video camera and the like. As the package shape of LED, there have been developed various package shapes suited for applications, such as bullet-shaped lamp, surface mounting type and the like. With respect to, in particular, white LED, its application to lighting is being pushed forward and there is high expectation as an alternate light source for conventional incandescent lamp, halogen lamp, fluorescent lamp, etc. However, for the wide spread thereof, higher luminance and improved light source efficiency are needed.

Ordinarily, LED is encapsulated with a transparent encapsulant comprising an epoxy resin, a silicone resin or the like, in order to protect the semiconductor device accommodated inside. Of the materials for encapsulant, the epoxy resin, in particular, has high adhesivity and high handleablity, is inexpensive, and is a material suitable for practical use; therefore, it is in wide use for encapsulation of LED. Meanwhile, the encapsulant for LED is required to have high light resistance in association with the above-mentioned move of LED to shorter wavelength. Further, in association with the move of LED to higher luminance, the encapsulant for LED is strongly required to have high heat resistance capable of withstanding the heat generated by the LED element.

Conventional epoxy resins such as bisphenol A type glycidyl ether and the like, used as a component of encapsulant tend to be deteriorated owing to the move to shorter wavelength or the heat generation of LED device. Consequently, there is a problem that the resin gives rise to yellowing, inviting a reduction in LED luminance and a change in LED color tone.

Various investigations have been made in order to achieve the above tasks. For example, light resistance of resin was slightly increased by adding an alicyclic epoxy to a hydrogenated bisphenol A type glycidyl ether (JP 2003-73452 A). However, the resulting resin has no sufficient weather resistance practically and further has lower heat resistance, causing discoloration. Also, it was attempted to further add, to the resin, a phosphorus-based antioxidant. In this case, an effect of suppressing the discoloration caused by heat was seen but there was a reduction in light resistance.

With respect to polycyclic epoxy compounds, there is a case in which an epoxy compound having only one epoxy group, such as 1-adamantylglycidyl ether was produced; however, there is no case in which an epoxy compound having two or more epoxy groups was produced at a high yield at a high purity.

As the conventional process for producing 1-adamantylglycidyl ether, there is known a process which comprises reacting 1-adamantanol with epichlorohydrin in the presence of a catalytic amount of tin tetra-chloride and then allowing sodium hydroxide to act on the reaction product to obtain 1-adamantylglycidyl ether (The Journal of Organic Chemistry USSR, Vol. 27, No. 6, pp. 1089-1092, 1991).

The process gives a yield of 61% which is not bad. In this process, however, tin tetra-chloride (which is a Lewis acid) is used as the catalyst. For the safety reason of the catalyst, the solvent usable is limited to low-polarity solvents such as halides. Hence, in production of 1-adamantylglycidyl ether, when the starting raw material is changed from 1-adamantanol to an adamantanepolyol having two or more hydroxyl groups (which has very low solubility in low-polar solvents), the reactivity thereof is not certain. Further, there is a fear that epichlorohydrin itself polymerizes in the presence of an acid such as Lewis acid and the polymerizate remains as an impurity. As a process for obtaining a glycidyl ether from an alcohol, there is generally considered a process which comprises reacting an alcohol with an alkali metal or the like to synthesize an alcoholate and contacting the alcoholate with epichlorohydrin or epibromohydrin. However, there is no case in which this process has been applied to any polycyclic hydroxy compound having two or more hydroxyl groups.

DISCLOSURE OF THE INVENTION

Each of the cured material obtained by curing a polycyclic hydrocarbon compound contains a polycyclic hydrocarbon skeleton in the molecule has superior optical properties and heat resistance. In the applications fields of such cured materials where the above properties are required, however, there are also required other properties which are different depending upon individual applications. In order to satisfy such diversified requirements, it is essential to develop a novel curable compound containing a polycyclic hydrocarbon skeleton.

In other words, the method of curing a curable compound containing a polycyclic hydrocarbon skeleton, to obtain a resin, is promising as a useful means for obtaining a resin superior in optical properties and heat resistance; however, such curable compounds currently known are limited and accordingly their applications are limited as well at the present stage.

In order to diversify the technique being employable, the present invention aims at providing a novel curable compound containing a polycyclic hydrocarbon skeleton in the molecule, which is useful industrially.

The present inventors made a study in order to achieve the above aim. As a result, it was found that novel curable polycyclic hydrocarbon compounds obtained by introducing, into a polycyclic hydrocarbon compound, oxetanyl group and/or epoxy group as polymerizable functional group can achieve the above aim.

These compounds, when cured, give a cured material high in optical properties and light resistance. It was further found that these compounds give a small shrinkage when cured and, therefore, can be suitably used as an adhesive or an encapsulant for semiconductor laser, both requiring optical properties, high heat resistance, etc.

The present invention has been completed based on these findings.

The present invention is as described below.

[1] A curable polycyclic compound represented by the following formula (1):

(1)

{wherein A is a di- to hexa-valent group derived from a polycyclic hydrocarbon compound; $R^1$ is an alkyl group of 1 to 4 carbon atoms, a perfluoroalkyl group of 1 to 4 carbon atoms, or a fluorine atom; n is an integer of 0 to 2; m is an integer of 2 to 4; and Y is a group represented by the following formula (2):

(2)

(wherein $R^2$ and $R^3$ are each independently a hydrogen atom, a fluorine atom or an alkyl group of 1 to 4 carbon atoms; $R^4$ is a methyl group or an ethyl group; and p is an integer of 0 to 4), or a group represented by the following formula (3):

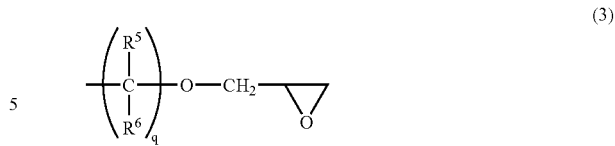

(3)

(wherein $R^5$ and $R^6$ are each independently a hydrogen atom, a fluorine atom or an alkyl group of 1 to 4 carbon atoms; and q is an integer of 0 to 4)}.

[2] A curable polycyclic compound according to [1], wherein the formula (1) is the following formula (4):

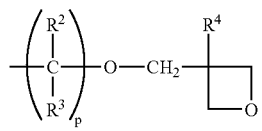

(4)

{wherein $R^1$ is an alkyl group of 1 to 4 carbon atoms, a perfluoroalkyl group of 1 to 4 carbon atoms, or a fluorine atom; a is an integer of 0 to 2; b is an integer of 0 to 2; and Y is a group represented by the following formula (2):

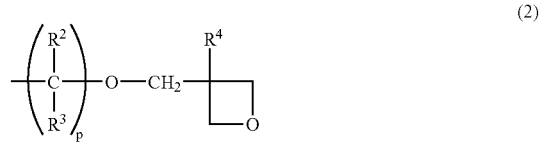

(2)

(wherein $R^2$ and $R^3$ are each independently a hydrogen atom, a fluorine atom or an alkyl group of 1 to 4 carbon atoms; $R^4$ is a methyl group or an ethyl group; and p is an integer of 0 to 4), or a group represented by the following formula (3):

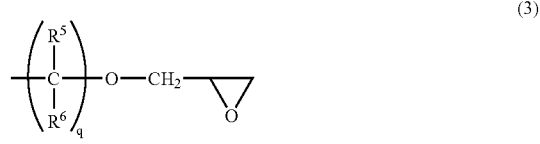

(3)

(wherein $R^5$ and $R^6$ are each independently a hydrogen atom, a fluorine atom or an alkyl group of 1 to 4 carbon atoms; and q is an integer of 0 to 4)}.

[3] A curable polycyclic compound according to [2], wherein, in the formula (4), a, p and q are 0 (zero).

[4] A curable polycyclic compound according to [1], wherein the content of the halogen molecule or halogen ion contained as an impurity is 100 to 2,000 ppm.

[5] A curable polycyclic compound represented by the general formula (6) or (7):

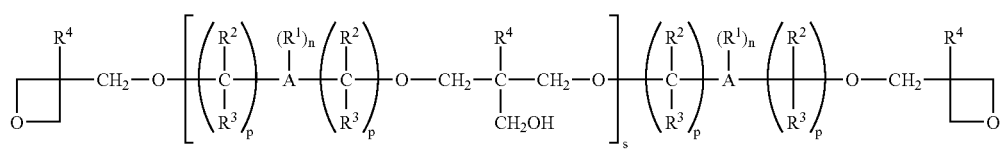

(6)

{wherein A, $R^1$, $R^2$, $R^3$, n and p have the same definitions as in the formula (1); and s is an integer of 1 to 3}

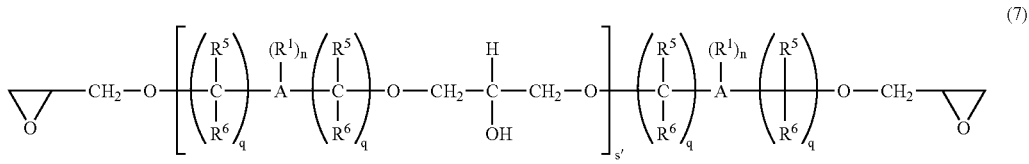

{wherein A, $R^1$, $R^5$, $R^6$, n and q have the same definitions as in the formula (1); and s' is an integer of 1 to 3}.

[6] A curable composition characterized by comprising a curable polycyclic compound set forth in any of [1] to [3] and a curing agent.

[7] A curable composition according to [6], wherein the curable polycyclic compound is a compound represented by the following formula (4):

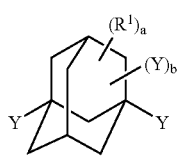

{wherein $R^1$ is an alkyl group of 1 to 4 carbon atoms, a perfluoroalkyl group of 1 to 4 carbon atoms, or a fluorine atom; a is an integer of 0 to 2; b is an integer of 0 to 2; and Y is a group represented by the following formula (3):

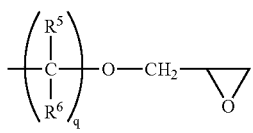

(wherein $R^5$ and $R^6$ are each independently a hydrogen atom, a fluorine atom or an alkyl group of 1 to 4 carbon atoms; and q is an integer of 0 to 4)}.

[8] An encapsulant for light-emitting diode, comprising a curable composition set forth in [6] or [7].

[9] A light-emitting diode encapsulated by an encapsulant set forth in [8].

[10] A process for producing a polycyclic epoxy compound represented by the following formula (8):

{wherein A is a di- to hexa-valent group derived form a polycyclic hydrocarbon compound; $R^1$ is an alkyl group of 1 to 4 carbon atoms, a perfluoroalkyl group of 1 to 4 carbon atoms, or a fluorine atom; n is an integer of 0 to 2; m is an integer of 2 to 4; and Z is a group represented by the above formula (3):

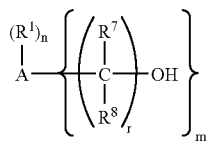

(wherein $R^5$ and $R^6$ are each independently a hydrogen atom, a fluorine atom or an alkyl group of 1 to 4 carbon atoms; and q is an integer of 0 to 4)}, which process is characterized by comprising the following steps (a) to (c):

a step (a) of reacting a polycyclic hydroxy compound represented by the following formula (9):

{wherein A, $R^1$, n and m have the same definitions as in the formula (8); $R^7$ and $R^8$ are each independently a hydrogen atom, a fluorine atom or an alkyl group of 1 to 4 carbon atoms; and r is an integer of 0 to 4}, with an alkali metal, an alkaline earth metal or an organometal compound containing such a metal to obtain an alcoholate, a step (b) of reacting the alcoholate obtained in the step (a), with an allyl group-containing compound represented by the following formula (10):

$$X-CH_2-CH=CH_2 \quad (10)$$

(wherein X is a halogen atom or a sulfonyloxy group) to obtain a polycyclic allyl compound represented by the following formula (11):

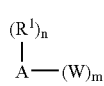

[wherein A, $R^1$, n and m have the same definitions as in the formula (8); and W is a group represented by the following formula (12):

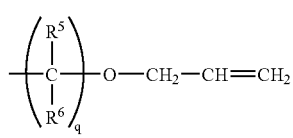

{wherein $R^5$, $R^6$ and q have the same definitions as in the formula (3)}], and a step (c) of oxidizing the polycyclic allyl compound obtained in the step (b).

[11] A polycyclic allyl compound represented by the following formula (11):

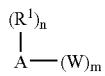
(11)

{wherein A is a di- to hexa-valent group derived from a polycyclic hydrocarbon compound; $R^1$ is an alkyl group of 1 to 4 carbon atoms, a perfluoroalkyl group of 1 to 4 carbon atoms, or a fluorine atom; n is an integer of 0 to 2; m is an integer of 2 to 4; and W is a group represented by the following formula (12):

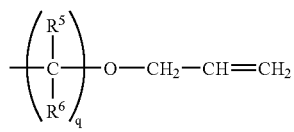
(12)

(wherein $R^5$ and $R^6$ are each independently a hydrogen atom, a fluorine atom or an alkyl group of 1 to 4 carbon atoms; and q is an integer of 0 to 4)}.

In each of the compounds represented by the above general formulas, when each group of $R^1$ to $R^8$, A, Y, X, Z and W is bonded in plurality in the molecule, they may be the same group or different groups.

As a raw material for adhesive or encapsulant, there have been used aliphatic curable compounds containing oxetanyl group or epoxy group, such as hydrogenated bisphenol A type and the like, and aromatic curable compounds containing oxetanyl group or epoxy group, such as bisphenol A type, novolac type and the like. Cured materials obtained from the former compounds have a problem of low heat resistance. Cured materials obtained from the latter compounds have a problem of low light resistance. The cured materials obtained from the latter compounds are low in transparency particularly in a short-wavelength region and, accordingly, when irradiated with an ultraviolet light, cause color development with the lapse of time and show a reduction in mechanical properties. Further, the cured materials obtained from the latter compounds have a problem of low refractive index.

In contrast, the cured materials obtained from the curable polycyclic compounds of the present invention are less in these problems.

The curable polycyclic compounds of the present invention are characterized by giving a cured material superior in optical properties, heat resistance and light resistance and being small shrinkage when cured. Therefore, the compounds can be suitably used as a raw material for various plastic substrates, a raw material for coating, a raw material for adhesive, a raw material for encapsulant, etc.

The cured material of the curable composition of the present invention is superior in light resistance, heat resistance, etc. and has high adhesivity to light-emitting diode. Therefore, the curable composition of the present invention is suitable as an encapsulant for short-wavelength LED (e.g. near-ultraviolet LED or white LED), etc.

BEST MODE FOR CARRYING OUT THE INVENTION

The curable polycyclic compounds of the present invention are represented by the above-shown formula (1), wherein oxetanyl group and/or epoxy group each represented by group —Y is bonded to carbon atoms of a polycyclic hydrocarbon skeleton. Since the group —Y has a chemical structure containing an ether bond, the compounds can be produced easily by an ordinary chemical reaction.

In the formula (1), A is a di- to hexa-valent group derived from a polycyclic hydrocarbon compound. As the group A, there can be mentioned di- to hexa-valent groups derived from adamantane, norbornane, bicyclooctane, bicyclononane, tetrahydrodicyclopentadiene, 1-ethyladamantane, 1-ethylnorbornane, 1-ethylbicyclooctane, 1-ethylbicyclononane, 1-ethyltetrahydrodicyclopentadiene, 5,7-dimethyladamantane, 1,4-dimethylnorbornane, 1,5-dimethylbicyclooctane, 1,5-dimethylbicyclononane, 1,5-dimethyltetrahydrodicyclopentadiene, 1-fluoroadamantane, 1-fluoronorbornane, 1-fluorobicyclooctane, 1-fluorobicyclononane, 1-fluorotetrahydrodicyclopentadiene, 1-trifluoromethyladamantane, 1-trifluoromethylnorbornane, 1-trifluoromethylbicyclooctane, 1-trifluoromethylbicyclononane, 1-trifluoromethyltetrahydrodicyclopentadiene, 1,3-difluoroadamantane, 1,4-difluoronorbornane, 1,5-difluorobicyclooctane, 1,5-difluorobicyclononane, 1,5-difluorotetrahydrodicyclopentadiene, etc.

Particularly preferred are di- to hexa-valent groups derived from adamantane having a stiff skeleton. Here, the di- to hexa-valent group derived from a polycyclic hydrocarbon compound means a group which has been formed by elimination of 2 to 6 hydrogen atoms from the polycyclic hydrocarbon skeleton of a polycyclic hydrocarbon compound and wherein the hydrogen-eliminated sites of the polycyclic hydrocarbon skeleton have become bonds (free valences). There is no particular restriction as to the sites of the bonds on the skeleton.

In the formula (1), $R^1$ means an alkyl group of 1 to 4 carbon atoms, a perfluoroalkyl group of 1 to 4 carbon atoms, or a fluorine atom. As the alkyl group, there can be mentioned methyl group, ethyl group, propyl group, isopropyl group, butyl group, etc. As the perfluoroalkyl group, there can be mentioned perfluoromethyl group, perfluoroethyl group, perfluorobutyl group, etc. Of these groups, methyl group is preferred as $R^1$ for the easy synthesis of the compound of the formula (1). n, which indicates the number of $R^1$ present in the molecule of the compound of the formula (1), is an integer of 0 to 2. n is preferably 2 for the easy synthesis of the compound of the formula (1) and the high heat resistance of a cured material obtained by curing of the compound of the formula (1).

When n is 2, two $R^1$s may be the same or different from each other. The two $R^1$s are preferably the same for the easy synthesis of the compound of the formula (1).

When n is 1 or 2, there is no particular restriction as to the site(s) to which $R^1$(s) bonds (bond), as long as the site(s) is (are) different from the sites to which oxetanyl group or epoxy group bonds.

In the formula (1), Y indicates a group represented by the formula (2) or (3). Incidentally, $R^2$ and $R^3$ of the formula (2) or $R^5$ and $R^6$ of the formula (3) are each independently a hydrogen atom, a fluorine atom or an alkyl group of 1 to 4 carbon atoms. The alkyl group of 1 to 4 carbon atoms has the same meaning as substituting group of 1 to 4 carbon atoms, of $R^1$. $R^4$ is a methyl group or an ethyl group.

p and q are each an integer of 0 to 4. p and q are preferably an integer of 0 or 1, more preferably an integer of 0, for the easy synthesis of the compound of the formula (1) and the good heat resistance of the compound. m, which indicates the number of the bonding group —Y which bonds to A, is an integer of 2 to 4. m is preferably 2 or 3, more preferably 2 for the high heat resistance and high flexibility of the cured material obtained. As to the bonding sites of the group —Y, it is preferred that at least two groups —Y bond to bridge head carbons; when m is 3 or 4, there is no particular restriction as to the bonding site(s) of remaining group(s) —Y.

In the formula (2), $R^4$ is a methyl group or an ethyl group.

As preferred specific examples of the curable polycyclic compound represented by the formula (1), there can be mentioned polycyclic hydrocarbon compounds having oxetanyl group, such as 1,3-bis[(3-ethyloxetan-3-yl)methoxy]adamantane, 2,5-bis[(3-ethyloxetan-3-yl)methoxy]norbornane, 2,6-bis[(3-ethyloxetan-3-yl)methoxy]bicyclooctane, 2,7-bis[(3-ethyloxetan-3-yl)methoxy]bicyclononane, 2,7-bis[(3-ethyloxetan-3-yl)methoxy]tetrahydrodicyclopentadiene, 5,7-dimethyl-1,3-bis[(3-ethyloxetan-3-yl)methoxy]adamantane, 1,4-dimethyl-2,5-bis[(3-ethyloxetan-3-yl)methoxy]norbornane, 1,5-dimethyl-2,6-bis[(3-ethyloxetan-3-yl)methoxy]bicyclooctane, 1,5-dimethyl-2,7-bis[(3-ethyloxetan-3-yl)methoxy]bicyclononane, 1,5-dimethyl-2,7-bis[(3-ethyloxetan-3-yl)methoxy]tetrahydrodicyclopentadiene, 1,3,5-tris[(3-ethyloxetan-3-yl)methoxy]adamantane, 2,3,5-tris[(3-ethyloxetan-3-yl)methoxy]norbornane, 2,4,6-tris[(3-ethyloxetan-3-yl)methoxy]bicyclooctane, 2,4,7-tris[(3-ethyloxetan-3-yl)methoxy]bicyclononane, 2,5,7-tris[(3-ethyloxetan-3-yl)methoxy]tetrahydrodicyclopentadiene, 1,3-bis[(3-ethyloxetan-3-yl)methoxymethyl]adamantane, 2,5-bis[(3-ethyloxetan-3-yl)methoxymethyl]norbornane, 2,6-bis[(3-ethyloxetan-3-yl)methoxymethyl]bicyclooctane, 2,7-bis[(3-ethyloxetan-3-yl)methoxymethyl]bicyclononane, 2,7-bis[(3-ethyloxetan-3-yl)methoxymethyl]tetrahydrodicyclopentadiene, 1,3,5-tris[(3-ethyloxetan-3-yl)methoxymethyl]adamantane, 2,3,5-tris[(3-ethyloxetan-3-yl)methoxymethyl]norbornane, 2,4,6-tris[(3-ethyloxetan-3-yl)methoxymethyl]bicyclooctane, 2,4,7-tris[(3-ethyloxetan-3-yl)methoxymethyl]bicyclononane, 2,5,7-tris[(3-ethyloxetan-3-yl)methoxymethyl]tetrahydrodicyclopentadiene and the like.

There can also be mentioned polycyclic hydrocarbon compounds having epoxy group, such as 1,3-bis(glycidyloxy)adamantane, 2,5-bis(glycidyloxy)norbornane, 2,6-bis(glycidyloxy)bicyclooctane, 2,7-bis(glycidyloxy)bicyclononane, 2,7-bis(glycidyloxy)tetrahydrodicyclopentadiene, 5,7-dimethyl-1,3-bis(glycidyloxy)adamantane, 1,4-dimethyl-2,5-bis(glycidyloxy)norbornane, 1,5-dimethyl-2,6-bis(glycidyloxy)bicyclooctane, 1,5-dimethyl-2,7-bis(glycidyloxy)bicyclononane, 1,5-dimethyl-2,7-bis(glycidyloxy)tetrahydrodicyclopentadiene, 1,3,5-tris(glycidyloxy)adamantane, 2,3,5-tris(glycidyloxy)norbornane, 2,4,6-tris(glycidyloxy)bicyclooctane, 2,4,7-tris(glycidyloxy)bicyclononane, 2,5,7-tris(glycidyloxy)tetrahydrodicyclopentadiene, 1,3-bis(glycidyloxymethyl)adamantane, 2,5-bis(glycidyloxymethyl)norbornane, 2,6-bis(glycidyloxymethyl)bicyclooctane, 2,7-bis(glycidyloxymethyl)bicyclononane, 2,7-bis(glycidyloxymethyl)tetrahydrodicyclopentadiene, 1,3,5-tris(glycidyloxymethyl)adamantane, 2,3,5-tris(glycidyloxymethyl)norbornane, 2,4,6-tris(glycidyloxymethyl)bicyclooctane, 2,4,7-tris(glycidyloxymethyl)bicyclononane, 2,5,7-tris(glycidyloxymethyl)tetrahydrodicyclopentadiene and the like.

Of these compounds, particularly preferred for the easy production and the capability of giving a cured material of high heat resistance are polycyclic hydrocarbon compounds having oxetanyl group, such as 1,3-bis[(3-ethyloxetan-3-yl)methoxy]adamantane, 2,5-bis[(3-ethyloxetan-3-yl)methoxy]norbornane, 2,6-bis[(3-ethyloxetan-3-yl)methoxy]bicyclooctane, 2,7-bis[(3-ethyloxetan-3-yl)methoxy]bicyclononane, 2,7-bis[(3-ethyloxetan-3-yl)methoxy]tetrahydrodicyclopentadiene, 1,3,5-tris[(3-ethyloxetan-3-yl)methoxy]adamantane, 2,3,5-tris[(3-ethyloxetan-3-yl)methoxy]norbornane, 2,4,6-tris[(3-ethyloxetan-3-yl)methoxy]bicyclooctane, 2,4,7-tris[(3-ethyloxetan-3-yl)methoxy]bicyclononane, 2,5,7-tris[(3-ethyloxetan-3-yl)methoxy]tetrahydrodicyclopentadiene and the like; and polycyclic hydrocarbon compounds having epoxy group, such as 1,3-bis(glycidyloxy)adamantane, 2,5-bis(glycidyloxy)norbornane, 2,6-bis(glycidyloxy)bicyclooctane, 2,7-bis(glycidyloxy)bicyclononane, 2,7-bis(glycidyloxy)tetrahydrodicyclopentadiene, 1,3,5-tris(glycidyloxy)adamantane, 2,3,5-tris(glycidyloxy)norbornane, 2,4,6-tris(glycidyloxy)bicyclooctane, 2,4,7-tris(glycidyloxy)bicyclononane, 2,5,7-tris(glycidyloxy)tetrahydrodicyclopentadiene and the like.

Of the present curable polycyclic compounds represented by the formula (1), particularly preferred are compounds represented by the following formula (4), having an adamantane skeleton and also having oxetanyl group or epoxy group, for the easy synthesis and good properties, etc.

(4)

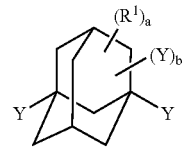

In the above formula, $R^1$ is an alkyl group of 1 to 4 carbon atoms, a perfluoroalkyl group of 1 to 4 carbon atoms, or a fluorine atom; a is an integer of 0 to 2; and b is an integer of 0 to 2.

Y is a group represented by the following formula (2):

(2)

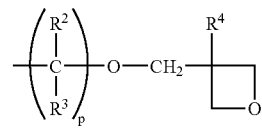

or a group represented by the following formula (3):

(3)

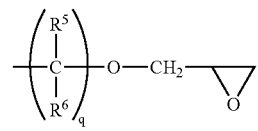

In the above formulas, $R^2$, $R^3$, $R^5$ and $R^6$ are each independently a hydrogen atom, a fluorine atom or an alkyl group of 1 to 4 carbon atoms. $R^4$ is a methyl group or an ethyl group. p and q are each an integer of 0 to 4.

Of the curable adamantane compounds represented by the formula (4), preferred are those curable adamantane compounds wherein both p and q are 0 (zero), for good physical properties, etc. As preferred specific examples of the compounds, there can be mentioned adamantane compounds having oxetanyl group, such as 1,3-bis[(3-ethyloxetan-3-yl)methoxy]adamantane, 5,7-dimethyl-1,3-bis[(3-ethyloxetan-3-yl)methoxy]adamantane, 1,3,5-tris[(3-ethyloxetan-3-yl)methoxy]adamantane and the like; and adamantane compounds having epoxy group, such as 1,3-bis(glycidyloxy)adamantane, 5,7-dimethyl-1,3-bis(glycidyloxy)adamantane, 1,3,5-tris(glycidyloxy)adamantane and the like.

Of these compounds, particularly preferred are adamantane compounds having oxetanyl group, such as 1,3-bis[(3-ethyloxetan-3-yl)methoxy]adamantane, 1,3,5-tris[(3-ethyloxetan-3-yl)methoxy]adamantane and the like, and adamantane compounds having epoxy group, such as 1,3-bis(glycidyloxy)adamantane, 1,3,5-tris(glycidyloxymethyl)adamantane and the like, for the easy production and the high heat resistance of the cured material obtained.

As to the process for production of each curable polycyclic compound of the present invention, there is no particular restriction. However, it can be produced preferably by the following processes.

(First Production Process)

(a) In the first production process, a polycyclic hydroxy compound having at least two hydroxyl groups, represented by the following formula (9):

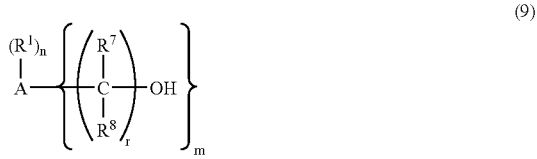

(9)

[wherein A, $R^1$, n and m have the same definitions as given in the formula (8); $R^7$ and $R^8$ are each independently a hydrogen atom, a fluorine atom or an alkyl group of 1 to 4 carbon atoms; and r is an integer of 0 to 4] is converted into a metal alcoholate; then, the metal alcoholate is reacted with an oxetane compound or an epoxy compound each having eliminatable group; thereby, a curable polycyclic compound of the present invention can be obtained.

With respect to the eliminatable group, there is no particular restriction as long as it is a group which reacts with an nucleophilic reagent (particularly an alcoholate anion in the present invention) and is eliminated as an anion. As the eliminatable group, there can generally be used a halogen atom such as chlorine atom, bromine atom, iodine atom or the like; or, a sulfonyloxy group such as benzenesulfonyloxy group, p-toluenesulfonyloxy group, p-brominated benzenesulfonyloxy group, methanesulfonyloxy group, trifluoromethanesulfonyloxy group or the like.

As specific examples of the raw material compound represented by the formula (9), there can be mentioned 1,3-adamantanediol, 2,5-norbornanediol, 2,6-bicyclooctanediol, 2,7-bicyclononanediol, 2,7-tetrahydrodicyclopentadienediol, 5-ethyl-1,3-adamantanediol, 1-ethyl-2,5-norbornanediol, 1-ethyl-2,6-bicyclooctanediol, 1-ethyl-2,7-bicyclononanediol, 1-ethyl-2,7-tetrahydrodicyclopentadienediol, 5,7-dimethyl-1,3-adamantanediol, 1,4-dimethyl-2,5-norbornanediol, 1,5-dimethyl-2,6-bicyclooctanediol, 1,5-dimethyl-2,7-bicyclononanediol, 1,5-dimethyl-2,7-tetrahydrodicyclopentadienediol, 1,3,5-adamantanetriol, 1,3,6-adamantanetriol, 2,3,5-norbornanetriol, 2,4,6-bicyclooctanetriol, 2,4,7-bicyclononanetriol, 2,5,7-tetrahydrodicyclopentadienetriol, 7-ethyl-1,3,5-adamantanetriol, 1-ethyl-2,3,5-norbornanetriol, 1-ethyl-2,4,6-bicyclooctanetriol, 1-ethyl-2,4,7-bicyclononanetriol, 1-ethyl-2,5,7-tetrahydrodicyclopentadienetriol, 1,3,5,7-adamantanetetraol, 1,2,3,5-norbornanetetraol, 1,2,4,6-bicyclooctanetetraol, 1,2,4,7-bicyclononanetetraol, 1,2,5,7-tetrahydrodicyclopentadienetetraol, 1,3-bis(hydroxymethyl)adamantane, 2,5-bis(hydroxymethyl)norbornane, 2,6-bis(hyroxymethyl)bicyclooctane, 2,7-bis(hydroxymethyl)bicyclononane, 2,7-bis(hydroxymethyl)tetrahydrodicyclopentadiene, 1,3,5-tris(hydroxymethyl)adamantane, 1,3-bis(hydroxyperfluoromethyl)adamantane, 2,5-bis(hydroxyperfluoromethyl)norbornane, 2,6-bis(hydroxyperfluoromethyl)bicyclooctane, 2,7-bis(hydroxyperfluoromethyl)bicyclononane, and 2,7-bis(hydroxyperfluoromethyl)tetrahydrodicyclopentadiene.

The polycyclic hydroxy compound represented by the formula (9), when the A of the formula (9) is a group derived form adamantane, can be produced easily by a method of oxidizing adamantane or an alkyladamantane.

Or, the compound of the formula (9) can be obtained easily by hydrolyzing a halogenated adamantane.

As the above-mentioned method for oxidation, there can be employed, for example, an oxidation method using chromic acid, disclosed in JP 1967-16621 A and JP 1990-104553 A; an oxidation method using a ruthenium compound and a hypochlorite, disclosed in JP 2000-219646 A and JP 2001-26563 A; and an oxidation method using hydroxyphthalimide as a catalyst, disclosed in JP 1996-38909 A or JP 1997-327626 A and JP 1998-286467 A.

As the above-mentioned method for hydrolysis, there can be employed, for example, a method for hydrolysis of brominated adamantane, disclosed in JP 1990-196744 A and JP 1991-118342 A.

When, the A of the formula (9) is a group derived from norbornane, bicyclooctane, bicyclononane or tetrahydrodicyclopentadiene, an alcohol compound can be synthesized by using, as a raw material, norbornene, bicyclooctene, bicyclononene or dicyclopentadiene and subjecting it to acid catalyzed addition of water, as described in Stand und Entwicklungstendenzen in der Chemie der Epoxydharze, Kunststoffe, Nos. 3 & 4, 1967.

When p is 1 to 4, there is a method which comprises reacting a polycyclic hydrocarbon compound such as adamantane with a boron trifluoride-ether complex and fuming sulfuric acid in 95% concentrated sulfuric acid to give rise to dicarboxylation and then reducing the dicarboxylation product with a reducing agent such as lithium aluminum hydride, as described in Journal of Medicinal Chemistry, Vol. 18, No. 7 (1975).

Or, the alcohol compound can be easily obtained by reacting a polycyclic hydrocarbon compound (e.g. adamantane) with vinyl chloride, sulfuric anhydride and concentrated nitric acid in concentrated sulfuric acid to give rise to dimethylcarboxylation and then reducing the dimethylcarboxylation product with a reducing agent (e.g. lithium aluminum hydride), as described in Izvestia Akademii Nauk, Seriya Khimicheskaya, No. 7, pp. 1612 to 1615 (1992).

As the oxetane compound having eliminatable group, which is reacted with the metal alcoholate of the polycyclic hydroxy compound of the formula (9), there can be mentioned, for example, p-toluenesulfonic acid ester of 3-alkyl- 3-hydroxymethyloxetane. The synthesis method of this oxetane compound is disclosed in Spanish Patent No. 2073995. Specifically explaining, the oxetane compound can be easily synthesized by reacting a 3-alkyl-3-hydroxymethyloxetane with a sulfonyl chloride compound represented by $RSO_2Cl$ (wherein R is, for example, a p-tolyl group) in the presence of an appropriate basic compound (e.g. pyridine) in an organic solvent at 0° C. to room temperature (25° C.).

As the epoxy compound having eliminatable group, there can be mentioned, for example, epichlorohydrin and epibromohydrin.

The alcoholate of the polycyclic hydroxy compound represented by the formula (9) can be produced by reacting the compound with a basic compound in a solvent. As the basic compound, there is ordinarily used an alkali metal, an alkaline earth metal or an organometal compound containing such a metal (such a metal or compound is hereinafter referred to as alkali metal or the like). As the alkali metal or the like, there can be mentioned alkali metals such as sodium and the like; alkali metal hydrides such as sodium hydride and the like; alkali metal hydroxides such as sodium hydroxide, potassium hydroxide and the like; alkaline earth metals such as magnesium, calcium and the like; organometal compounds such as methyllithium, butyllithium and the like; and so forth.

The use amount of the basic compound is appropriately determined depending upon the number of m of the formula (9). Ordinarily, the use amount is preferably 0.5 to 5.0 mols, particularly preferably 1.0 to 1.5 mols relative to 1 mol of the hydroxyl group contained in the polycyclic hydroxy compound represented by the formula (9).

As the solvent used in the above reaction, there can be mentioned, for example, aromatic hydrocarbon solvents such as toluene, xylene and the like; and aprotic polar solvents such as tetrahydrofuran, N,N-dimethylformamide, N,N-dimethylacetamide, dimethyl sulfoxide, hexamethylphosphoric triamide, N-methylpyrrolidone and the like.

As to the use amount of the solvent, there is no particular restriction. However, too small an amount results in reduced reactivity and too large an amount is not preferred for economy; therefore, the solvent is used in an amount of 1 to 500 mols, preferably 2 to 300 mols relative to 1 mol of hydroxyl group of the polycyclic hydroxy compound.

As to the reaction temperature, there is no particular restriction. However, when there is used an alkali metal or an alkali metal hydride as the basic compound, the temperature is preferably 0 to 80° C. and, when there is used an alkali metal hydroxide, the temperature is preferably 30 to 130° C. The reaction time differs depending upon the reaction temperature used, but is ordinarily about 1 to 10 hours.

After the polycyclic hydroxy compound has been converted into an alcoholate, there is added thereto an oxetane compound having eliminatable group or an epoxy compound having eliminatable group, whereby a curable polycyclic compound of the present invention can be obtained. In this case, the use amount of the oxetane compound having eliminatable group or the epoxy compound having eliminatable group may be appropriately determined depending upon the number of the m of the polycyclic hydroxy compound represented by the formula (9) to be produced. Ordinarily, the use amount is preferred to be 0.5 to 5.0 mols, particularly 1.0 to 1.5 mols relative to 1 mol of the hydroxyl group contained in the polycyclic compound represented by the formula (9).

The temperature of the above reaction is not particularly restricted but is preferred to be 0 to 130° C. The reaction may be conducted by using a pressure apparatus (e.g. an autoclave), as necessary. The reaction time differs depending upon the reaction temperature used but is ordinarily about 1 to 48 hours. An additive such as potassium iodide or the like may be used for a increased reaction rate.

After the above reaction, the reaction mixture is neutralized with an acid such as hydrochloric acid or the like and then a purification treatment is conducted as necessary, whereby a curable polycyclic compound (1) of the present invention can be obtained.

(Second Production Process)

A polycyclic epoxy compound, which is a curable polycyclic compound of the general formula (1) wherein Y is a group represented by the formula (3), can be obtained by converting a polycyclic hydroxy compound represented by the general formula (9) into an alcoholate, reacting the alcoholate with an allyl compound having eliminatable group, and allowing an oxidizing agent to act on the reaction product.

This second production process is described in more detail. In this process, a polycyclic epoxy compound represented by the following formula (8) is produced.

In the formula (8), A, $R^1$, n and m have the same definitions as in the general formula (1).

In the formula (8), Z is the following group represented by the above-shown formula (3).

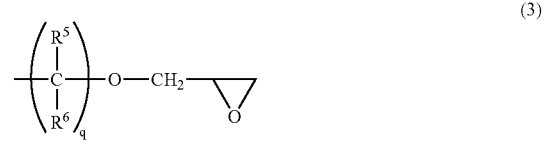

The process for producing the compound of the formula (8) comprises the following steps (a) to (c). In this process, a novel polycyclic allyl compound produced in the steps (a) and (b) is used as an intermediate, whereby an intended product (8) can be obtained easily at a high yield at a high purity. The steps (a) to (c) are explained in detail below.

In the production process of the present invention, first in the step (a), a polycyclic hydroxy compound represented by the following formula (9) is reacted with a basic compound, preferably an alkali metal, an alkaline earth metal or an organometal compound containing such a metal, to obtain an alcoholate.

This step is conducted according to the same manner as in the first production process.

In the formula (9), A, $R^1$, n and m have the same definitions as in the formula (8); $R^7$ and $R^8$ are each independently a hydrogen atom, a fluorine atom or an alkyl group of 1 to 4 carbon atoms; and r is an integer of 0 to 4.

In the present process, in the step (b), the alcoholate of a polycyclic hydroxy compound, obtained in the step (a) is reacted with an allyl group-containing compound represented by the following formula (10) to obtain a polycyclic allyl compound represented by the following formula (11).

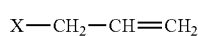  (10)

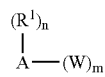  (11)

In the formula (10), X is a halogen atom or a sulfonyloxy group. In the formula (11), A, R¹, n and m have the same definitions as in the formula (8); and W is a group represented by the following formula (12).

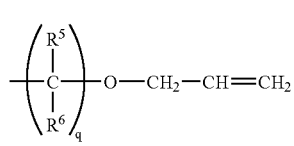  (12)

{wherein $R^5$, $R^6$ and q have the same definitions as in the formula (3)}.

As the allyl group-containing compound represented by the formula (10), there can be used a reagent or an easily obtainable industrial raw material with no restriction. As specific examples thereof, there can be mentioned vinyl chloride, vinyl bromide, vinyl iodide, allyl chloride, allyl bromide, allyl iodide, allyl benzenesulfonate, allyl trifluoromethanesulfonate, allyl toluenesulfonate, allyl brominated benzenesulfonate, allyl methanesulfonate. Allyl chloride, allyl bromide and allyl iodide are used preferably in view of the availability, operability, reactivity, etc. The use amount of the allyl group-containing compound is 1 mole relative to 1 mol of the hydroxyl group contained in the polycyclic hydroxy compound (9) which is a raw material for alcoholate; however, in view of the hindrance by the remaining basic compound, etc., the amount is preferably 1.0 to 5.0 mols, more preferably 1.05 to 3.0 mols. As the method for contacting the alcoholate of the polycyclic hydroxy compound (9) with the allyl group-containing compound (10), there is preferred, in view of the heat generated, etc., a method of dropping the allyl group-containing compound into the alcoholate of the polycyclic hydroxy compound, or a method of dropping the alcoholate of the polycyclic hydroxy compound (9) into the allyl group-containing compound (10). That is, there is preferred a method of dropping either one raw material to the other raw material. There is no particular restriction as to the temperature during dropping. However, too high a dropping temperature produces a large amount of impurity, and too low a dropping temperature results in a reduced reaction rate. The dropping temperature is ordinarily −40 to 100° C., preferably −30 to 90° C. The time of the reaction differs depending upon the reaction temperature employed but is ordinarily about 0.5 to 10 hours from the completion of dropping.

The above-obtained polycyclic allyl compound is washed with water, then subjected to an operation such as solvent removal by distillation and is recovered as a crude polycyclic ally compound of a liquid state. This crude compound may be used per se but is preferred to be purified by distillation, silica gel column chromatography or the like.

The polycyclic allyl compound obtained is a compound (an intermediate) which is a direct raw material for intended polycyclic epoxy compound. The difference between the intermediate and the intended compound is simply that the group —Z in the formula (8) has been changed to a group —W (specifically explaining, epoxy group (as the group Z) has been changed to vinyl group). Therefore, the A, $R^1$, $R^5$, $R^6$, m, n and q in the polycyclic allyl compound are the same as in the formula (8).

As preferred specific examples of the polycyclic allyl compound represented by the formula (11), there can be mentioned 1,3-bis(2-propenyloxy)adamantane, 2,5-bis(2-propenyloxy)norbornane, 2,6-bis(2-propenyloxy)bicyclooctane, 2,7-bis(2-propenyloxy)bicyclononane, 2,7-bis(2-propenyloxy)tetrahydrodicyclopentadiene, 5,7-dimethyl-1,3-bis(2-propenyloxy)adamantane, 1,4-dimethyl-2,5-bis(2-propenyloxy)norbornane, 1,5-dimethyl-2,6-bis(2-propenyloxy)bicyclooctane, 1,5-dimethyl-2,7-bis(2-propenyloxy)bicyclononane, 1,5-dimethyl-2,7-bis(2-propenyloxy)tetrahydrodicyclopentadiene, 1,3,5-tris(2-propenyloxy)adamantane, 2,3,5-tris(2-propenyloxy)norbornane, 2,4,6-tris(2-propenyloxy)bicyclooctane, 2,4,7-tris(2-propenyloxy)bicyclononane, 2,5,7-tris(2-propenyloxy)tetrahydrodicyclopentadiene, 1,3-bis(2-propeneyloxymethyl)adamantane, 2,5-bis(2-propeneyloxymethyl)norbornane, 2,6-bis(2-propeneyloxymethyl)bicyclooctane, 2,7-bis(2-propeneyloxymethyl)bicyclononane, 2,7-bis(2-propeneyloxymethyl)tetrahydrodicyclopentadiene, 1,3,5-tris(2-propenyloxymethyl)adamantane, 2,3,5-tris(2-propenyloxymethyl)norbornane, 2,4,6-tris(2-propenyloxymethyl)bicyclooctane, 2,4,7-tris(2-propenyloxymethyl)bicyclononane, and 2,5,7-tris(2-propenyloxymethyl)tetrahydrodicyclopentadiene.

In the present process, in the step (c), the polycyclic allyl compound is oxidized to convert the vinyl group (the group —W) into epoxy group (group —Z), whereby an intended polycyclic epoxy compound is obtained.

The oxidation includes oxidation by organic peroxide (e.g. peracid such as peracetic acid, perbenzoic acid, m-chloroperbenzoic acid or the like, or peroxide such as dimethyldioxirane or the like) in solvent, oxidation by oxygen and oxidation by chromic acid. The oxidation by organic peroxide is simple in view of the conversion and the non-use of catalyst. Of the above organic peroxides, m-chloroperbenzoic acid is particularly preferable in view of the availability and safety. The use amount of the organic peroxide is 1 mol relative to 1 mol of the allyl group contained in the polycyclic allyl compound, but is ordinarily 1 to 5 mols, preferably 1.05 to 3.0 mols. As the solvent used in the above reaction, there are mentioned halogenated solvents such as dichloromethane, chloroform, carbon tetrachloride and the like; aliphatic hydrocarbon solvents such as hexane, heptane, cyclohexane and the like; aromatic hydrocarbon solvents such as toluene, xylene and the like; and so forth. There is no particular restriction as to the use amount of the solvent. However, too small an amount results in reduced reactivity and too large an amount is uneconomical; therefore, the solvent is used in an amount of 1 to 500 times, preferably 2 to 300 times the mass of the polycyclic allyl compound used. The temperature of the reaction is not restricted particularly. However, too high a temperature results in an increased amount of impurity and too low a temperature results in a reduced reaction rate. Hence, the temperature is ordinarily −10 to 100° C., preferably 0 to 60° C. The reaction time differs depending upon the reaction temperature employed and the use amount of organic peroxide, but is ordinarily about 5 to 100 hours.

The above-obtained polycyclic epoxy compound (8) is subjected to washing with water and distillation for solvent removal. The resulting crude polycyclic epoxy compound has a high purity per se, but is subjected to purification by distillation, silica gel column chromatography or the like to obtain a polycyclic epoxy compound of higher purity.

The curable polycyclic compound (1) of the present invention has a polycyclic hydrocarbon skeleton and accordingly gives a cured material having superior optical properties and heat resistance. Further, the curable polycyclic compound (1) of the present invention contains oxetane group or epoxy group introduced into the polycyclic hydrocarbon skeleton and accordingly has a feature of showing a small shrinkage during the polymerization. Therefore, the curable polycyclic compound (1) of the present invention is suitably used particularly in the encapsulant for light-emitting diode.

In JP 2003-73452 A, it is described that, when bisphenol A or hydrogenated bisphenol A is reacted with epichlorohydrin to produce a bisphenol A type epoxy resin or a hydrogenated bisphenol A type epoxy resin, the amount of chlorine remaining in the produced resin reaches 50,000 ppm.

When a curable polycyclic compound contains a large amount of halogen molecule or halogen ion, the resin obtained by curing the compound is extremely low in heat resistance and light resistance.

Accordingly, when a curable polycyclic compound containing a large amount of halogen molecule or halogen ion is used in applications such as encapsulant and the like, the resin formed causes deterioration and can not be used stably.

In the curable polycyclic compound of the present invention, the halogen molecule or halogen ion contained therein as an impurity can be reduced to a low level of 100 to 2,000 ppm, preferably 200 to 2,000 ppm by selecting the production conditions and conducting purification. Therefore, the curable polycyclic compound of the present invention is suited for applications requiring heat resistance and weather resistance, such as encapsulant and the like.

In order to analyze the halogen molecule or halogen ion contained as an impurity in the curable polycyclic compound of the present invention, a known method can be employed. As the method, there can be mentioned, for example, a quantitative analysis method of organic chlorine (a quantitative analysis method of saponifiable chlorine by ISO 4583) and a quantitative analysis method of inorganic chlorine (a method by ISO 4573).

The curable polycyclic compound of the present invention can be used suitably, for example, as a raw material for various plastic substrates, a raw material for coating, a raw material for adhesive and a raw material for encapsulant. The curable polycyclic compound, when subjected to homopolymerization, gives a cured material wherein the above-mentioned properties of the compound are utilized.

It is possible that the curable polycyclic compound of the present invention is mixed with other curable compound reactive therewith (hereinafter, referred to as co-reacting agent) and the resulting curable mixture is subjected to co-polymerization to obtain a cured material.

There is no particular restriction as to the co-reacting agent as long as it is reactive with the curable polycyclic compound of the present invention. As the co-reacting agent, there may be appropriately selected a co-reacting agent which can allow a cured material obtained to have properties required in an intended application. As such a co-reacting agent, there can be mentioned oxetane compounds, epoxy compounds and cation-polymerizable monomers. As specific examples, there can be mentioned oxetane compounds such as xylylenedioxetane, 3-ethyl-3-hydroxymethyloxetane, 3-ethyl-3-phenoxymethyloxetane and the like; bisphenol A type epoxy compounds such as bisphenol A diglycidyl ether and the like; bisphenol F type epoxy compounds such as bisphenol F diglycidyl ether and the like; hydrogenated bisphenol A type epoxy compounds such as hydrogenated bisphenol A diglycidyl ether and the like; epoxy compounds such as phenolic novolac type epoxy compound, glycidylamine type epoxy compound, naphthalene type epoxy compound, silicon type epoxy compound and the like; and cation-polymerizable monomers such as isobutyl vinyl ether, N-vinylcarbazole, p-methoxystyrene, isobutene and the like. These co-reacting agents can be used singly or in admixture of two or more kinds.

The composition of the curable mixture may be determined appropriately depending upon the application purpose. When the curable polycyclic compound is used for property improvement, the curable polycyclic compound is used in an amount of preferably 10 to 98% by mass, particularly preferably 20 to 95% by mass (the rest is the co-reacting agent) based on the total mass of the curable mixture obtained.

(Curing Agent)

There is no particular restriction as to the method for curing the curable polycyclic compound or the curable mixture between the compound and the co-reacting agent to obtain a cured material. There can be employed a known method.

The curable polycyclic compound or the curable mixture is mixed, as necessary, with various additives and stabilizers such as filler, coupling agent, flame retardant, ultraviolet absorber, infrared absorber, ultraviolet stabilizer, antioxidant, coloring inhibitor, antistatic agent, dye, pigment, perfume and the like, and then can be made into a cured material. The addition amount of such additives and stabilizers is determined by an ordinary method.

The curable polycyclic compound having oxetanyl group can be cured by cationic polymerization, using a curing agent as necessary.

The curable polycyclic compound having epoxy group can be cured by cationic polymerization, anionic polymerization or the like, using a curing agent as necessary. Here, the curing agent means a compound which has a functional group chemically reacting with oxetanyl group or epoxy group and which reacts with a compound having oxetanyl group or epoxy group to form a cured material.

As the curing agent, there can be used, with no restriction, compounds ordinarily used in curing of oxetanyl compound or epoxy compound. There can be mentioned, for example, phenol derivatives such as bisphenol A, bisphenol F, novolac resin and the like; acid anhydrides such as phthalic anhydride, maleic anhydride, tetrahydrophthalic anhydride, pyromellitic anhydride, 3-methyltetrahydrophthalic anhydride and the like; amine compounds such as m-phenylenediamine, diethylenetriamine, triethylenetetramine, xylenediamine, diaminodiphenylmethane and the like; and polyamides. Of these compounds, acid anhydrides are particularly preferable.

The preferred use amount of the curing agent is such an amount that the functional group of curing agent reacting with the oxetanyl group or epoxy group of curable polycyclic compound becomes 0.6 to 1.5 mols, preferably 0.8 to 1.2 mols per 1 mol of the oxetanyl group or epoxy group. When the proportion of the functional group of curing agent to the oxetanyl group or epoxy group is less than 0.6 or more than 1.4, the cured material obtained tends to be low in strength and water resistance.

As the cationic polymerization initiator, there can be used, with no restriction, those ordinarily used in curing of a compound having oxetanyl group or epoxy group. There can be mentioned, for example, protonic acids such as trifluoroacetic acid, trifluoromethanesulfonic acid, chlorosulfonic acid and the like; initiators selected from combinations of Lewis acid (e.g. boron trifluoride, tin tetrachloride, iron chloride, phosphorus pentafluoride, arsenic pentafluoride or antimony pentafluoride) and cation source (e.g. protonic acid, water or alcohol); cation-forming substances such as iodine and the like; and cationic photo-initiators such as diaryl iodonium salt (e.g. diphenyl iodonium hexafluorophosphate), triaryl sulfonium salt (e.g. triphenyl sulfonium hexafluorophosphate) and the like. The use amount of the cationic initiator is preferably 0.01 to 10 mols, more preferably 0.2 to 5 mols per 1 mol of the oxetanyl group or epoxy group of curable polycyclic compound.

As the anionic polymerization initiator, there can be used, with no restriction, those ordinarily used in curing of an epoxy compound. There can be mentioned, for example, tertiary amines such as dibutylmethylamine, diundecylmethylamine and the like. The use amount of the anionic polymerization initiator is such that the functional group of polymerization initiator reacting with the epoxy group of the curable polycyclic compound of the present invention becomes 0.01 to 10 mols, more preferably 0.2 to 5 mols per 1 mol of the epoxy group.

The curing agent may contain components other than mentioned above. The curing agent is preferred to contain a curing accelerator from the standpoint of, in particular, rapid formation of cured material. The curing accelerator is particularly effective when used in combination with the curing agent. As the curing accelerator, there can be mentioned, for example, tertiary amines such as triethylamine, tributylamine, pyridine, benzyldimethylamine, 1,8-diazabicyclo[5.4.0]undecene-7 and the like; organic acid salts thereof; imidazoles such as 2-methylimidazole, 2-ethyl-4-methylimidazole and the like; organic acid salts thereof; metal salts of organic acids, such as tin octylate and the like; amine salt of boron trifluoride; and quaternary phosphoric acid salts. Of these, preferably used from the standpoint of light resistance are quaternary phosphoric acid salts such as tetrabutylphosphonium diethylphosphorodithioate and the like. The preferred use amount of the curing accelerator is 0.1 to 5 parts by mass per 100 parts by mass of the curable polycyclic compound.

In the present invention, particularly preferred as the curable composition is, as described later, a composition which contains, as a curable polycyclic compound, a compound represented by the above-mentioned formula (4) wherein Y is a group represented by the formula (3), that is, an epoxy group-containing adamantane compound.

Description is made below on the specific form of a curable composition using such an epoxy group-containing adamantane compound.

The curable composition may contain an epoxy compound other than the epoxy group-containing adamantane compound (hereinafter, referred to as other epoxy compound), for improvement in adhesivity, electrical properties, workability for production, etc. As the other epoxy compound, there can be used a known epoxy compound with no restriction. As examples of preferably usable other epoxy compound, there can be mentioned phenol type glycidyl ethers such as bisphenol A glycidyl ether, brominated bisphenol A glycidyl ether, bisphenol C glycidyl ether, tetraglycidyl benzophenone, diglycidyl bisphenol F, triglycidyl-p-aminophenol, novolac type epoxy and the like; alicyclic glycidyl ethers such as diglycidyl cyclohexane-1,3-dicarboxylate, hydrogenated bisphenol A glycidyl ether, hydrogenated bisphenol A glycidyl ether and the like; alicyclic epoxys such as vinylcyclohexene dioxide, 7-oxabicyclo[4.1.0]hept-3-ylmethyl-7-oxabicyclo[4.1.0]heptane-3-carboxylate and the like; and glycidyl esters such as diglycidyl phthalate, diglycidyl tetrahydrophthalate, diglycidyl hexahydrophthalate, glycidyl dimerate, diglycidyl hexahydrophthalate, diglycidyl p-oxybenzoate and the like.

Of these other epoxy compounds, preferred are alicyclic epoxy compounds for the good light resistance. As examples of such alicyclic epoxy compounds, there can be mentioned alicyclic glycidyl ethers such as hydrogenated bisphenol A glycidyl ether, hydrogenated bisphenol A glycidyl ether and the like; and alicyclic epoxys such as vinylcyclohexene dioxide, 7-oxabicyclo[4.1.0]hept-3-ylmethyl-7-oxabicyclo[4.1.0]heptane-3-carboxylate and the like. Particularly preferred are alicyclic epoxys having 3,4-epoxycyclohexyl group. As an example thereof, there can be mentioned 7-oxabicyclo[4.1.0]hept-3-ylmethyl-7-oxabicyclo[4.1.0]heptane-3-carboxylate.

As to the content of the other epoxy compound, there is no particular restriction. However, the use amount is preferably 1 to 1,000 parts by mass relative to 100 parts by mass of the epoxy group-containing adamantane compound from the standpoint of good light resistance and heat resistance.

The curable composition can further contain, as necessary, a silicone compound (e.g. polydimethylsiloxane or polyphenylmethylsiloxane), a filler (e.g. calcium carbonate or magnesium oxide), a surfactant, a leveling agent, an anti-static agent, a light or heat stabilizer (e.g. ultraviolet absorber, antioxidant, hindered amine or hindered phenol), etc. for improved properties of cured material. The use amount of these additives is not restricted particularly but is preferably 1 to 1,000 parts by mass, particularly preferably 20 to 500 parts by mass relative to 100 parts by mass of the total amount of the epoxy group-containing adamantane compound and the other epoxy compound.

(Curable Composition)

Description is made below on a curable composition superior particularly as an encapsulant for LED device.

This curable composition is obtained by mixing a curable polycyclic compound (including an oligomer described later) of the present invention, preferably an epoxy group-containing adamantane compound, a curing agent and, as necessary, various optional components mentioned above. With respect to the mixing method therefor, when the curable polycyclic compound is an epoxy group-containing adamantane compound, it is generally preferred that the epoxy group-containing adamantane compound, a curing agent and optional components other than cationic polymerization initiator are mixed uniformly and lastly a cationic polymerization initiator is added, followed by uniform mixing.

The composition obtained is maintained under reduced pressure to give rise to defoaming, in order to allow the cured material obtained to have higher transparency.

The curable composition has a feature of being superior in light resistance, heat resistance, etc. and accordingly is usable preferably as an encapsulant for LED device. There is no particular restriction as to the method for using the curable composition in encapsulation of LED device. In general, there is mentioned a method which comprises bonding a LED device to a package by die bonding, inserting a pair of lead wires extending from the package, into the LED device to fix the LED device in the plastic-made package, pouring a curable composition of the present invention into the package, then curing the composition by heat or light, to conduct encapsulation.

For curing the composition by heat, there are, for example, a method of allowing the composition to stand in a heating oven for a given time and a method of mounting the composition on a belt conveyor or the like and passing it through a heating zone (e.g. on a plate heater). When the composition is used as an encapsulant for LED device and cured, the heating temperature is not particularly restricted as long as the LED device is not damaged at the temperature; however, the temperature is preferably 20 to 250° C., more preferably 80 to 200° C. The heating time is preferably 5 minutes to 48 hours. When the composition is cured by light, there can be used a known light source such as high-pressure mercury lamp, low-pressure mercury lamp, a metal halide lamp, a halogen lamp or the like. In that case, the light source, the irradiation dose and the irradiation time may be appropriately selected depending upon the composition of the curable composition used.

(Oligomer)

A high-quality cured material can be formed not only by the curable polycyclic compound of the present invention but also by a compound having a structure in which two to four molecules (these molecules may be the same or different) of the curable polycyclic compound of the present invention are polymerized or condensed as described below (since this compound can be seen as a dimer or tetramer, it is hereinafter referred to also as oligomer). The oligomer can be preferably used as a raw material for various plastic substrates, a raw material for coating, a raw material for adhesive, a raw material for encapsulant, etc.

The oligomer can be easily produced generally by a fusion method, an advanced method, a method which is called a two-step reaction method, or the following method wherein a monomer (a starting raw material) and an alcohol are subjected to addition polymerization. That is, the oligomer can be obtained by reacting a polycyclic hydroxy compound having at least two hydroxyl groups, represented by the following formula (9):

(9)

{wherein A, $R^1$, n and m have the same definitions as in the formula (8); $R^7$ and $R^8$ are each independently a hydrogen atom, a fluorine atom or an alkyl group of 1 to 4 carbon atoms; and r is an integer of 0 to 4} with a basic compound and an oxetane compound or an epoxy compound each having eliminatable group, simultaneously.

As the basic compound, there can be mentioned, for example, alkali metals such as sodium and the like; alkali metal hydrides such as sodium hydride and the like; and alkali metal hydroxides such as sodium hydroxide, potassium hydroxide and the like. The use amount of the basic compound is not particularly restricted; however, it is preferably 1.0 to 5.0 mols, particularly preferably 1.5 to 3.0 mols per 1 mol of the hydroxyl group contained in the polycyclic hydrocarbon compound represented by the formula (9).

The oxetane compound having eliminatable group can be exemplified by 3-alkyl-3-hydroxymethyloxetane p-toluenesulfonate. The synthesis method for the compound is disclosed in Spanish Patent No. 2073995.

Specifically explaining, the compound can be synthesized easily by reacting a 3-alkyl-3-hydroxymethyloxetane with a sulfonyl chloride compound represented by $RSO_2Cl$ (R is p-tolyl group or the like) in the presence of an appropriate basic compound (e.g. pyridine) in an organic solvent at 0° C. to room temperature (25° C.).

As the epoxy compound having eliminatable group, there can be mentioned, for example, epichlorohydrin and epibromohydrin.

As the solvent used in the above reaction, there can be mentioned, for example, aromatic hydrocarbon solvents such as toluene, xylene and the like; and aprotic polar solvents such as tetrahydrofuran, N,N-dimethylformamide, N,N-dimethylacetamide, dimethyl sulfoxide, hexamethylphosphoric triamide, N-methylpyrrolidone and the like.

In the above reaction, there are simultaneously added the compound of the formula (9), the basic compound, the oxetane compound or the epoxy compound each having eliminatable group and the solvent.

The reaction temperature is not particularly restricted but is preferably 0 to 130° C. The reaction may be conducted by using, as necessary, a pressure apparatus (e.g. an autoclave).

The reaction time differs depending upon the reaction temperature used but is ordinarily preferred to be about 1 to 48 hours. An additive such as potassium iodide or the like may be added for increased reaction rate.

After the completion of the reaction, the reaction mixture is neutralized with hydrochloric acid or the like and subjected to a purification treatment, whereby the above-mentioned oligomer can be obtained.

Examples of the general formula of the oligomer are shown by the following formula (6) and (7).

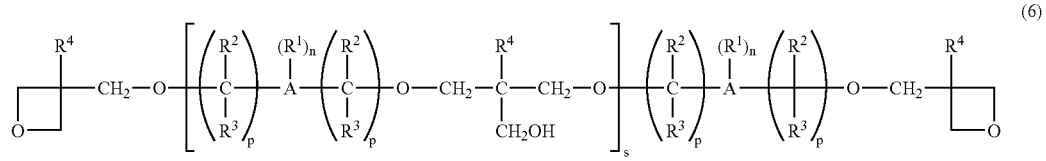

(6)

{wherein A, $R^1$, $R^2$, $R^3$, n and p have the same definitions as in the formula (1); and s is an integer of 1 to 3.}

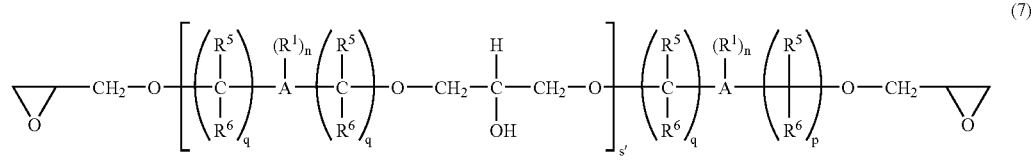

(7)

{wherein A, $R^1$, $R^5$, $R^6$, n and q have the same definitions as in the formula (1); and s' is an integer of 1 to 3.}
As preferable examples of the oligomer, there can be mentioned the followings.
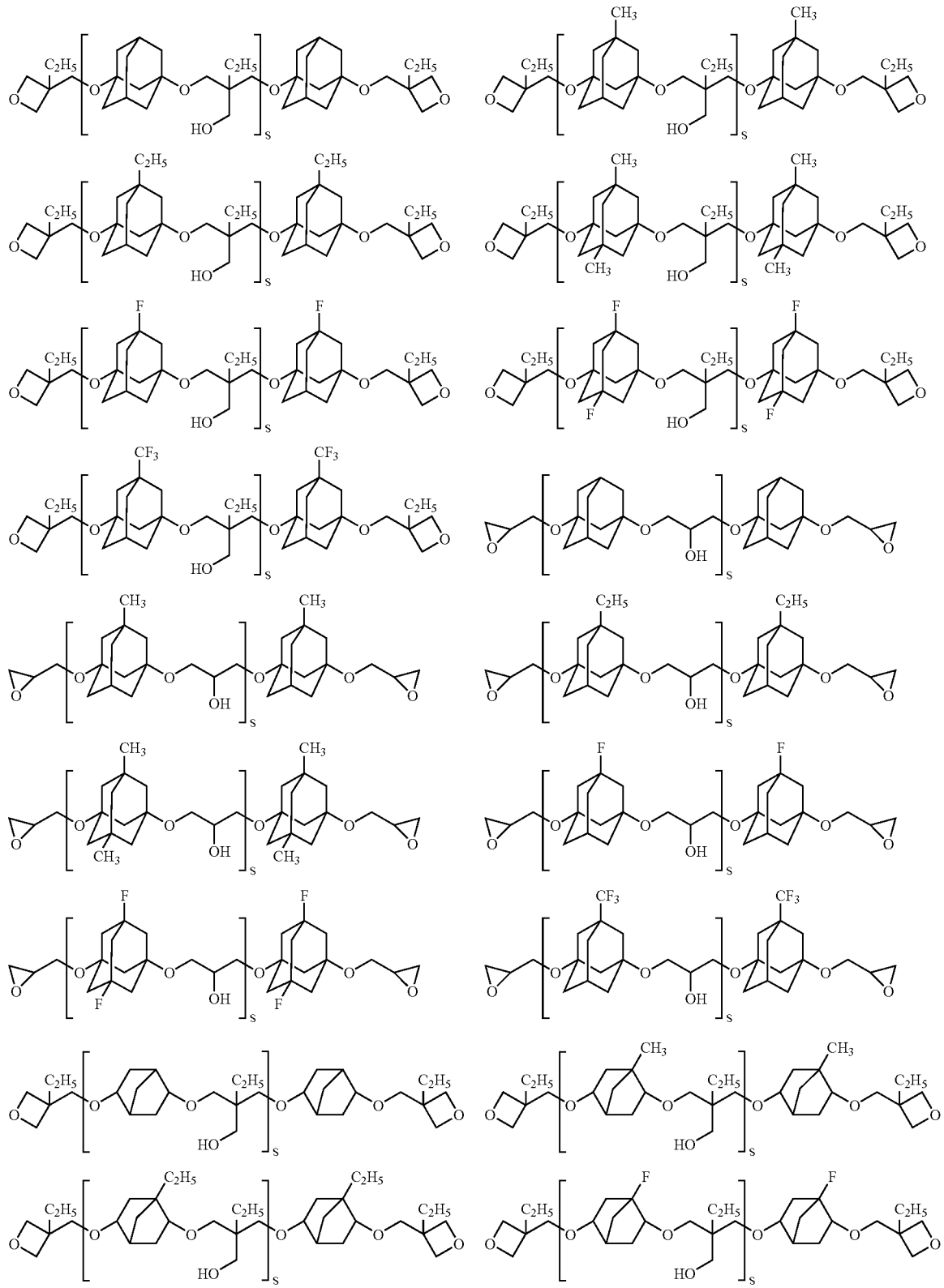

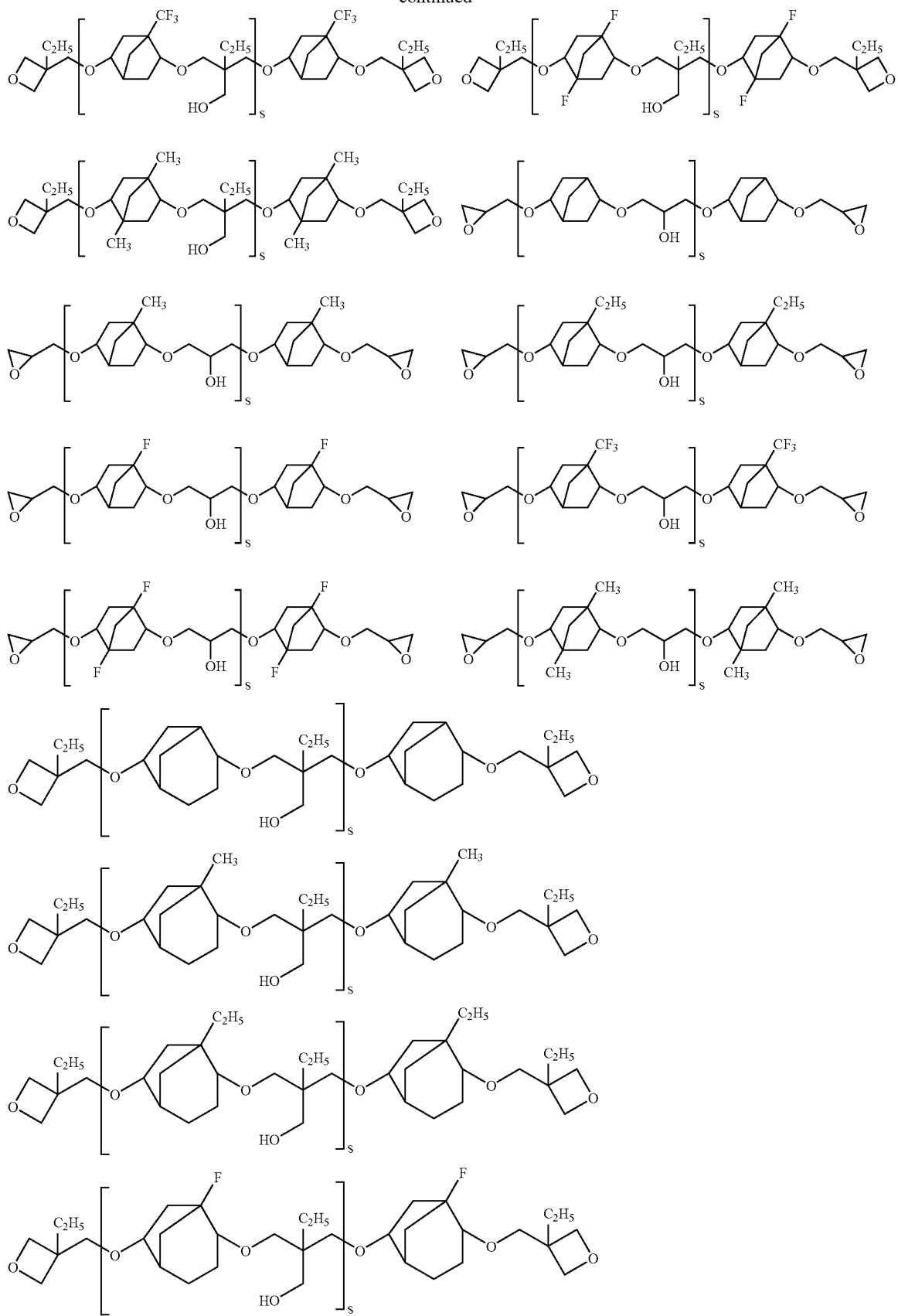

-continued
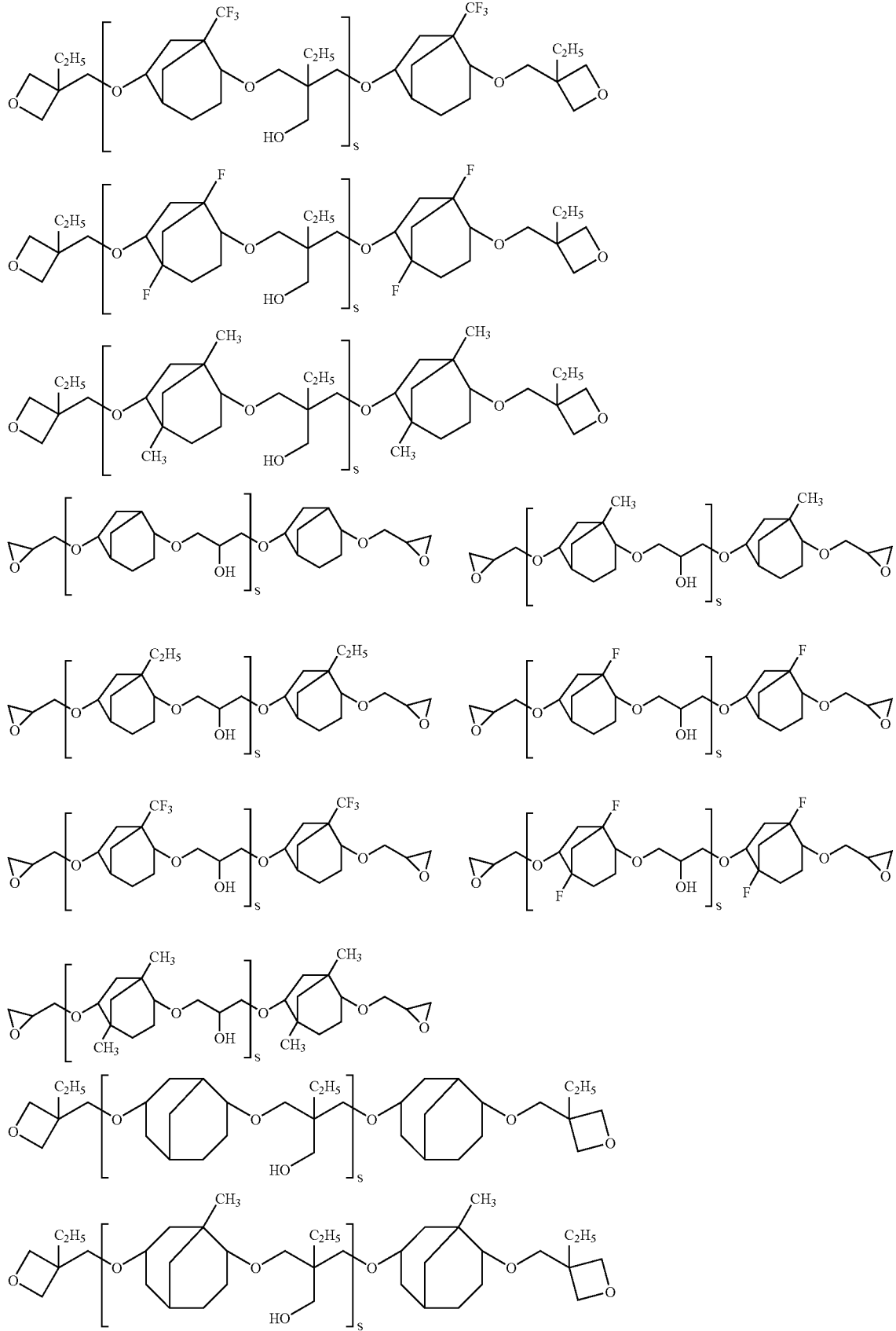

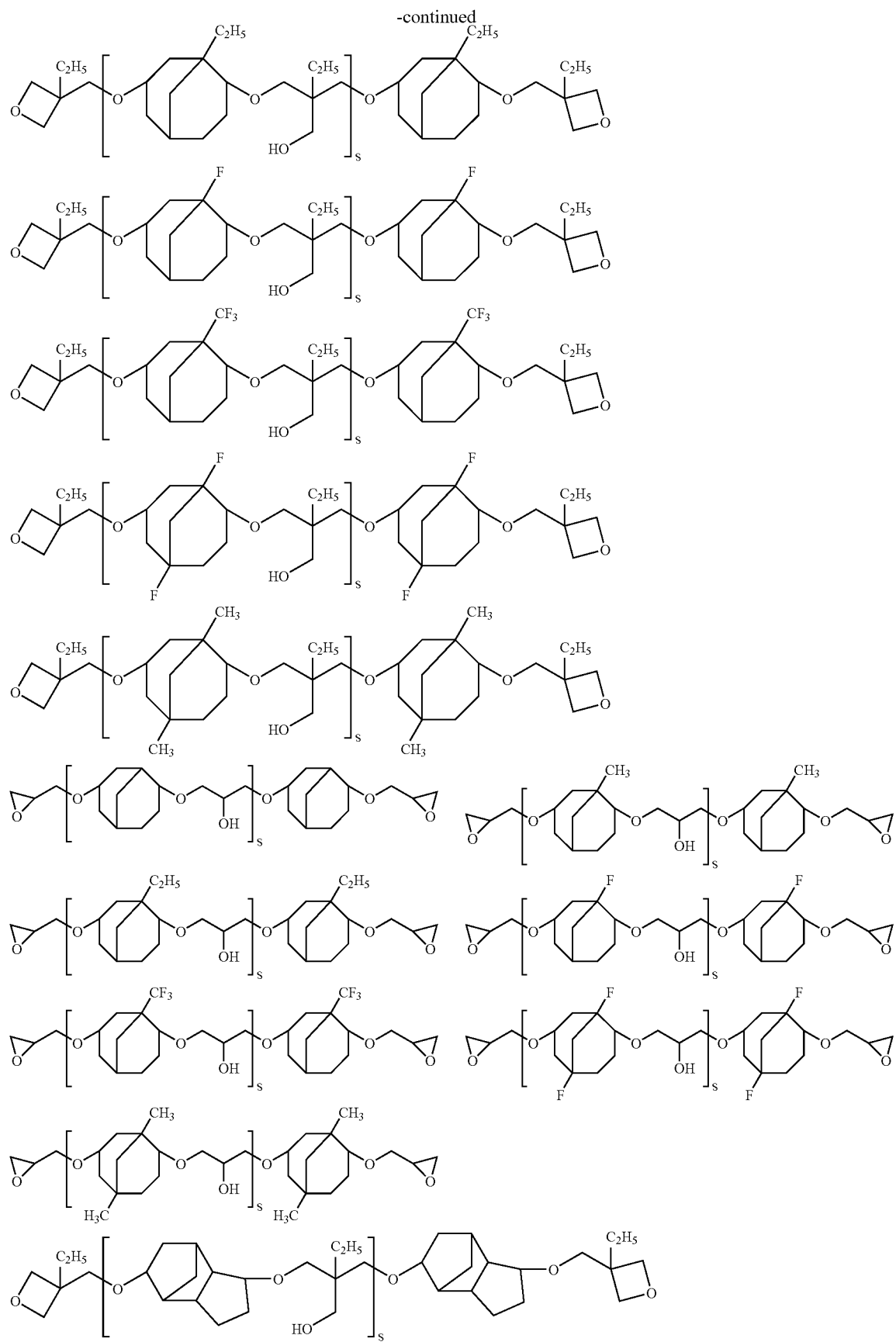

-continued
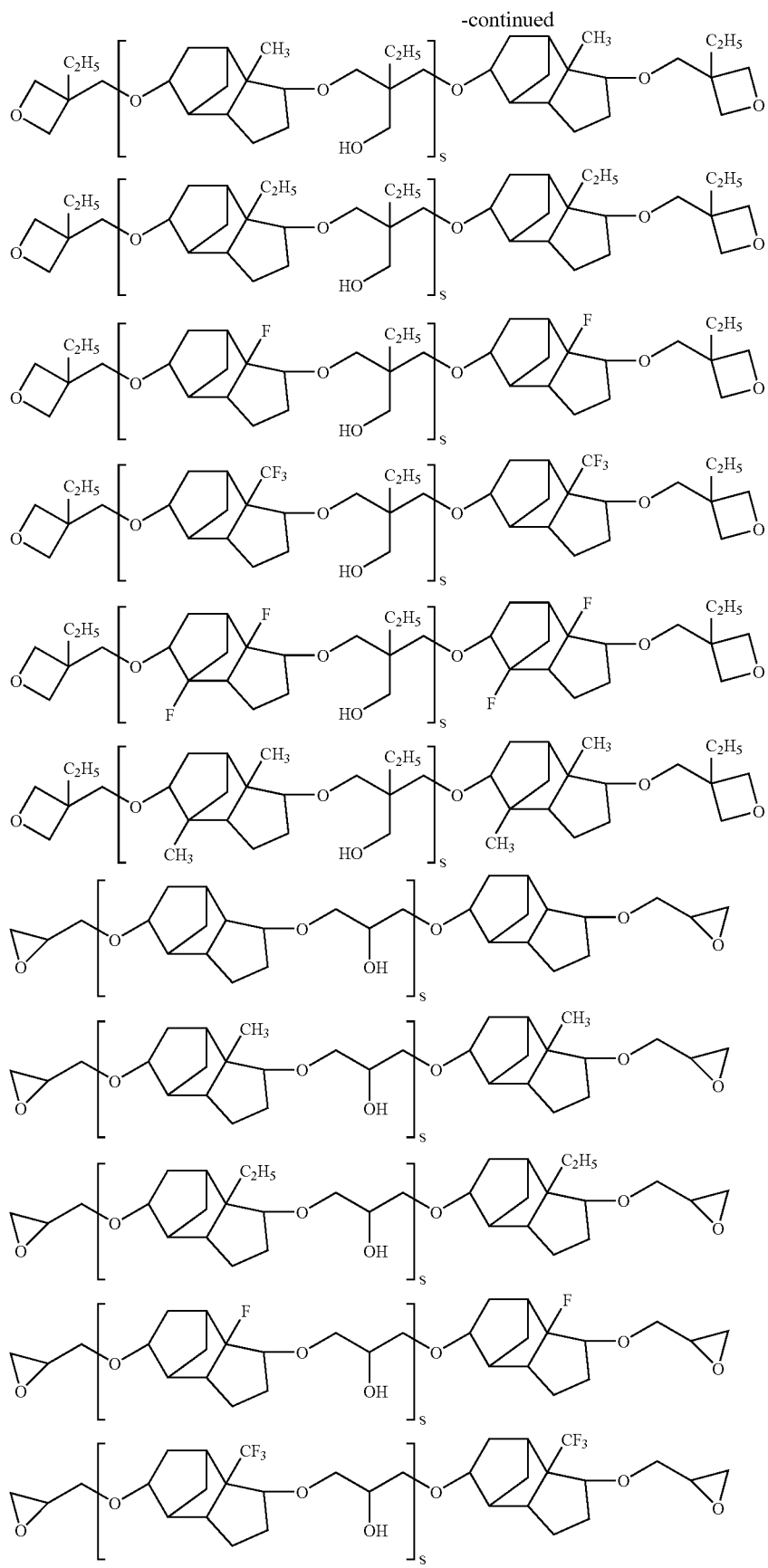

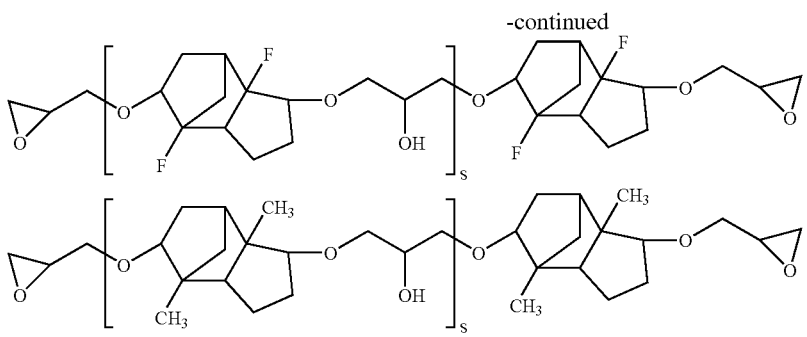

(in the above formulas, s is an integer of 1 to 3.)

EXAMPLES

The present invention is specifically described below by way of Examples. However, the present invention is in no way restricted to these Examples.

Example 1

Synthesis of 1,3-bis[(3-ethyloxetan-3-yl)methoxy]adamantane 300 ml of dehydrated tetrahydrofuran containing 16.8 g (0.1 mol) of 1,3-adamantanediol and 5.3 g (0.22 mol) of sodium hydride was stirred in a nitrogen atmosphere at the reflux temperature for 2 hours. Thereto was dropwise added 56.4 g (0.22 mol) of 3-ethyl-3-p-toluenesulfonyloxymethyloxetane. 36.5 g (0.22 mol) of potassium iodide was added. The resulting mixture was stirred at the reflux temperature for 12 hours. To the reaction mixture was added 200 ml of chloroform. The mixture was washed with water, and the chloroform layer was dried with magnesium sulfate.

The dried chloroform layer was subjected to distillation under reduced pressure for solvent removal, whereby was obtained a white solid and oily matter. This was purified by silica gel column chromatography to obtain 2.39 g (yield: 7.1%) of a white solid and oily matter. This compound was subjected to MASS spectrometry, $^1$H-NMR spectrometry and elemental analysis. From the results of the analyses, the compound was confirmed to be intended 1,3-bis[(3-ethyloxetan-3-yl)methoxy]adamantane. The results of analyses are shown below.

MASS (EI): molecular weight 336 (M$^+$)
$^1$H-NMR (TMS standard): δ 1.1-2.0 (m, 20H), 2.6-4.1 (m, 12H)
Elemental analysis: as $C_{20}H_{32}O_4$ Calculated: C, 71.39, H, 9.59. Measured: C, 71.76, H, 9.63.

The compound was measured for inorganic chlorine content by the method for determination of saponifiable chlorine, described in ISO 4583 and the method described in ISO 4573. The result was that the organic chlorine content was 210 ppm, the inorganic chlorine content was 10 ppm and the total chlorine content was 220 ppm.

Example 2

Synthesis of 2,5-bis[(3-ethyloxetan-3-yl)methoxy]norbornane 300 ml of dehydrated tetrahydrofuran containing 12.8 g (0.1 mol) of 2,5-norbornanediol and 5.3 g (0.22 mol) of sodium hydride was stirred in a nitrogen atmosphere at the reflux temperature for 2 hours. Thereto was dropwise added 56.4 g (0.22 mol) of 3-ethyl-3-p-toluenesulfonyloxymethyloxetane. 36.5 g (0.22 mol) of potassium iodide was added. The resulting mixture was stirred at the reflux temperature for 12 hours. To the reaction mixture was added 200 ml of chloroform. The chloroform layer was washed with water and then dried with magnesium sulfate. The dried chloroform layer was subjected to distillation under reduced pressure for solvent removal, whereby was obtained a white solid and oily matter. This was purified by silica gel column chromatography to obtain 1.39 g (yield: 4.71%) of a white solid and oily matter. This compound was subjected to MASS spectrometry, $^1$H-NMR spectrometry and elemental analysis. From the results of the analyses, the compound was confirmed to be intended 2,5-bis[(3-ethyloxetan-3-yl)methoxy]norbornane. The results of analyses are shown below.

MASS (EI): molecular weight 296 (M$^+$)
$^1$H-NMR (TMS standard): δ 1.1-2.0 (m, 16H), 2.6-4.1 (m, 12H)
Elemental analysis: as $C_{17}H_{28}O_4$ Calculated: C, 68.89, H, 9.52. Measured: C, 68.81, H, 9.62.

The compound was measured for inorganic chlorine content by the method for determination of saponifiable chlorine, described in ISO 4583 and the method described in ISO 4573. The result was that the organic chlorine content was 230 ppm, the inorganic chlorine content was 19 ppm and the total chlorine content was 249 ppm.

Example 3

Synthesis of 5,7-dimethyl-1,3-bis[(3-ethyloxetan-3-yl)methoxy]adamantane

An operation was conducted in the same manner as in Example 1 except that 16.8 g (0.10 mol) of 1,3-adamantanediol was replaced by 19.6 g (0.10 mol) of 5,7-dimethyl-1,3-adamantanediol, whereby was obtained 2.70 g (yield: 7.4%) of a white compound and oily matter. This compound was subjected to MASS spectrometry, $^1$H-NMR spectrometry and elemental analysis. From the results of the analyses, the compound was confirmed to be intended 5,7-dimethyl-1,3-bis[(3-ethyloxetan-3-yl)methoxy]adamantane. The results of analyses are shown below.

MASS (EI): molecular weight 364 (M$^+$)
$^1$H-NMR: δ 1.1-2.0 (m, 24H), 2.6-4.1 (m, 12H)
Elemental analysis: as $C_{22}H_{36}O_4$ Calculated: C, 72.49, H, 9.95. Measured: C, 72.87, H, 9.88.

The compound was measured for inorganic chlorine content by the method for determination of saponifiable chlorine, described in ISO 4583 and the method described in ISO 4573.

The result was that the organic chlorine content was 410 ppm, the inorganic chlorine content was 28 ppm and the total chlorine content was 438 ppm.

Example 4

Synthesis of 1,3,5-tris[(3-ethyloxetan-3-yl)methoxy]adamantane

An operation was conducted in the same manner as in Example 1 except that 16.8 g (0.10 mol) of 1,3-adamantanediol was replaced by 18.4 g (0.10 mol) of 1,3,5-adamantanetriol, the amount of sodium hydride was changed to 7.9 g (0.33 mol) and the amount of 3-ethyl-3-p-toluenesulfonyloxymethyloxetane was changed to 84.6 g (0.33 mol), whereby was obtained 1.92 g (yield: 4.4%) of a white compound and oily matter.

This compound was subjected to MASS spectrometry, $^1$H-NMR spectrometry and elemental analysis. As a result, the compound was confirmed to be intended 1,3,5-tri[(3-ethyloxetan-3-yl)methoxy]adamantane.

The results of analyses are shown below.

MASS (EI): molecular weight 436 ($M^+$)

$^1$H-NMR: δ 1.1-2.0 (m, 32H), 2.6-4.1 (m, 18H)

Elemental analysis: as $C_{25}H_{40}O_6$ Calculated: C, 68.78, H, 9.23. Measured: C, 68.56, H, 9.54.

The compound was measured for inorganic chlorine content by the method for determination of saponifiable chlorine, described in ISO 4583 and the method described in ISO 4573. The result was that the organic chlorine content was 360 ppm, the inorganic chlorine content was 40 ppm and the total chlorine content was 400 ppm.

Example 5

Synthesis of 1,3-bis(glycidyloxy)adamantane 300 ml of dehydrated tetrahydrofuran containing 16.8 g (0.1 mol) of 1,3-adamantanediol and 5.3 g (0.22 mol) of sodium hydride was stirred in a nitrogen atmosphere at the reflux temperature for 2 hours. Thereto was dropwise added 20.4 g (0.22 mol) of epichlorohydrin, followed by stirring at the reflux temperature for 12 hours. To the reaction mixture was added 200 ml of chloroform. The chloroform layer was washed with water and dried with magnesium sulfate. The dried chloroform layer was subjected to distillation under reduced pressure for solvent removal, to obtain oily matter. It was purified by silica gel column chromatography to obtain 1.79 g (yield: 6.4%) of oily matter.

This compound was subjected to MASS spectrometry, $^1$H-NMR spectrometry and elemental analysis. As a result, the compound was confirmed to be intended 1,3-bis(glycidyloxy)adamantane. The results of analyses are shown below.

MASS (EI): molecular weight 280 ($M^+$)

$^1$H-NMR: δ 1.1-2.5 (m, 14H), 2.5-4.1 (m, 10H)

Elemental analysis: as $C_{16}H_{24}O_4$ Calculated: C, 68.54, H, 8.63. Measured: C, 68.22, H, 8.85.

The compound was measured for inorganic chlorine content by the method for determination of saponifiable chlorine, described in ISO 4583 and the method described in ISO 4573. The result was that the organic chlorine content was 600 ppm, the inorganic chlorine content was 10 ppm and the total chlorine content was 610 ppm.

Example 6

Synthesis of 2,5-bis(glycidyloxy)norbornane 300 ml of dehydrated tetrahydrofuran containing 12.8 g (0.1 mol) of 2,5-norbrnanediol and 5.3 g (0.22 mol) of sodium hydride was stirred in a nitrogen atmosphere at the reflux temperature for 2 hours. Thereto was dropwise added 20.4 g (0.22 mol) of epichlorohydrin, followed by stirring at the reflux temperature for 12 hours. To the reaction mixture was added 200 ml of chloroform. The chloroform layer was washed with water and dried with magnesium sulfate. The dried chloroform layer was subjected to distillation under reduced pressure for solvent removal, whereby was obtained a white solid and oily matter. This was purified by silica gel column chromatography to obtain 1.20 g (yield: 5.0%) of a white solid and oily matter. This compound was subjected to MASS spectrometry, $^1$H-NMR spectrometry and elemental analysis. From the results of the analyses, the compound was confirmed to be intended 2,5-bis(glycidyloxy)norbornane. The results of analyses are shown below.

MASS (EI): molecular weight 240 ($M^+$)

$^1$H-NMR: δ 1.1-2.0 (m, 10H), 2.7-4.1 (m, 10H)

Elemental analysis: as $C_{13}H_{20}O_4$ Calculated: C, 64.98, H, 8.39. Measured: C, 64.92, H, 8.40.

The compound was measured for inorganic chlorine content by the method for determination of saponifiable chlorine, described in ISO 4583 and the method described in ISO 4573. The result was that the organic chlorine content was 530 ppm, the inorganic chlorine content was 27 ppm and the total chlorine content was 557 ppm.

Example 7

Synthesis of 5,7-dimethyl-1,3-bis(glycidyloxy)adamantane

An operation was conducted in the same manner as in Example 5 except that 16.8 g (0.10 mol) of 1,3-adamantanediol was replaced by 19.6 g (0.10 mol) of 5,7-dimethyl-1,3-adamantanediol, whereby was obtained 2.13 g (yield: 6.9%) of a white compound and oily matter. This compound was subjected to MASS spectrometry, $^1$H-NMR spectrometry and elemental analysis. As a result, the compound was confirmed to be intended 5,7-dimethyl-1,3-bis(glycidyloxy)adamantane. The results of analyses are shown below.

MASS (EI): molecular weight 308 ($M^+$)

$^1$H-NMR: δ 1.1-2.0 (m, 18H), 2.7-4.1 (m, 10H)

Elemental analysis: as $C_{18}H_{28}O_4$ Calculated: C, 70.10, H, 9.15. Measured: C, 70.35, H, 9.03.

The compound was measured for inorganic chlorine content by the method for determination of saponifiable chlorine, described in ISO 4583 and the method described in ISO 4573. The result was that the organic chlorine content was 710 ppm, the inorganic chlorine content was 12 ppm and the total chlorine content was 722 ppm.

Example 8

Synthesis of 1,3,5-tris(glycidyloxy)adamantane

An operation was conducted in the same manner as in Example 1 except that, in Example 5, 16.8 g (0.10 mol) of 1,3-adamantanediol was replaced by 18.4 g (0.10 mol) of 1,3,5-adamantanetriol, the amount of sodium hydride was changed to 7.9 g (0.33 mol), and the amount of epichlorohydrin was changed to 30.5 g (0.33 mol), to obtain 1.5 g (yield: 4.2%) of a white solid and oily matter. This compound was subjected to MASS spectrometry, $^1$H-NMR spectrometry and elemental analysis. As a result, the compound was confirmed to be intended 1,3,5-tris(glycidyloxy)adamantane. The results of analyses are shown below.

MASS (EI): molecular weight 352 (M$^+$)
$^1$H-NMR: δ 1.1-2.0 (m, 13H), 2.7-4.1 (m, 15H)
Elemental analysis: as $C_{19}H_{28}O_6$ Calculated: C, 64.75, H, 8.01. Measured: C, 65.11, H, 8.23.

The compound was measured for inorganic chlorine content by the method for determination of saponifiable chlorine, described in ISO 4583 and the method described in ISO 4573. The result was that the organic chlorine content was 550 ppm, the inorganic chlorine content was 23 ppm and the total chlorine content was 573 ppm.

Example 9

Synthesis of 2,3,5-tri(glycidyloxy)norbornane

An operation was conducted in the same manner as in Example 1 except that, in Example 6, 12.8 g (0.10 mol) of 2,5-norbornanediol was replaced by 14.4 g (0.10 mol) of 2,3,5-norbornanetriol, the amount of sodium hydride was changed to 7.9 g (0.33 mol), and the amount of epichlorohydrin was changed to 30.5 g (0.33 mol), to obtain 1.6 g (yield: 5.0%) of a white solid and oily matter. This compound was subjected to MASS spectrometry, $^1$H-NMR spectrometry and elemental analysis. As a result, the compound was confirmed to be intended 2,3,5-tris(glycidyloxy)norbornane. The results of analyses are shown below.

MASS (EI): molecular weight 312 (M$^+$)
$^1$H-NMR: δ 1.1-2.0 (m, 9H), 2.7-4.1 (m, 15H)
Elemental analysis: as $C_{16}H_{24}O_6$ Calculated: C, 61.52, H, 7.74. Measured: C, 61.50, H, 7.69.

The compound was measured for inorganic chlorine content by the method for determination of saponifiable chlorine, described in ISO 4583 and the method described in ISO 4573. The result was that the organic chlorine content was 670 ppm, the inorganic chlorine content was 34 ppm and the total chlorine content was 704 ppm.

Example 10

Synthesis of 1,3-bis(glycidyloxymethyl)adamantane 300 ml of dehydrated tetrahydrofuran containing 19.6 g (0.1 mol) of 1,3-bis(hydroxymethyl)adamantane and 5.3 g (0.22 mol) of sodium hydride was stirred in a nitrogen atmosphere at the reflux temperature for 2 hours. Thereto was dropwise added 20.4 g (0.22 mol) of epichlorohydrin, followed by stirring at the reflux temperature for 12 hours. To the reaction mixture was added 200 ml of chloroform, followed by washing with water. The chloroform layer was dried with magnesium sulfate. The dried chloroform layer was subjected to distillation under reduced pressure for solvent removal, whereby was obtained a white solid and oily matter.

This was purified by silica gel column chromatography to obtain 1.9 g (yield: 6.7%) of a white solid and oily matter.

This compound was subjected to MASS spectrometry, $^1$H-NMR spectrometry and elemental analysis. As a result, the compound was confirmed to be intended 1,3-bis(glycidyloxymethyl)adamantane. The results of analyses are shown below.

MASS (EI): molecular weight 308 (M$^+$)
$^1$H-NMR: δ 1.1-2.0 (m, 14H), 2.5-4.1 (m, 14H)
Elemental analysis: as $C_{18}H_{28}O_4$ Calculated: C, 70.10, H, 9.15. Measured: C, 70.36, H, 9.32.

The compound was measured for inorganic chlorine content by the method for determination of saponifiable chlorine, described in ISO 4583 and the method described in ISO 4573. The result was that the organic chlorine content was 800 ppm, the inorganic chlorine content was 20 ppm and the total chlorine content was 820 ppm.

Example 11

Synthesis of oligomer of
1,3-bis[(3-ethyloxetan-3-yl)methoxy]adamantane 56.4 g (0.22 mol) of 3-ethyl-3-p-toluenesulfonyloxymethyloxetane was added to 300 ml of dehydrated tetrahydrofuran containing 16.8 g (0.1 mol) of 1,3-adamantanediol and 5.3 g (0.22 mol) of sodium hydride, in a nitrogen atmosphere, followed by stirring at the reflux temperature for 2 hours. Thereto was added 36.5 g (0.22 mol) of potassium iodide, followed by stirring at the reflux temperature for 12 hours. To the reaction mixture was added 200 ml of chloroform. The chloroform layer was washed with water and then dried with magnesium sulfate. The dried chloroform layer was subjected to distillation under reduced pressure for solvent removal, to obtain a white solid and oily matter.

This was purified by silica gel column chromatography to obtain 5.39 g of a white solid and oily matter. This compound was subjected to gel permeation chromatography (hereinafter, referred to as GPC), which indicated a peak at around 660 to 680 (molecular weight) (Mw/Mn=1.11). From this result, the compound was confirmed to be a dimer of 1,3-bis[(3-ethyloxetan-3-yl)methoxy]adamantane.

The compound was measured for inorganic chlorine content by the method for determination of saponifiable chlorine, described in ISO 4583 and the method described in ISO 4573. The result was that the organic chlorine content was 220 ppm, the inorganic chlorine content was 20 ppm and the total chlorine content was 240 ppm.

Example 12

Synthesis of oligomer of
2,5-bis[(3-ethyloxetan-3-yl)methoxy]norbornane 56.4 g (0.22 mol) of 3-ethyl-3-p-toluenesulfonyloxymethyloxetane was added to 300 ml of dehydrated tetrahydrofuran containing 12.8 g (0.1 mol) of 2,5-norbornanediol and 5.3 g (0.22 mol) of sodium hydride, in a nitrogen atmosphere, followed by stirring at the reflux temperature for 2 hours. Thereto was added 36.5 g (0.22 mol) of potassium iodide, followed by stirring at the reflux temperature for 12 hours. To the reaction mixture was added 200 ml of chloroform. The chloroform layer was washed with water and then dried with magnesium sulfate. The dried chloroform layer was subjected to distillation under reduced pressure for solvent removal, to obtain a white solid and oily matter.

This was purified by silica gel column chromatography to obtain 6.01 g of a white solid and oily matter. This compound was subjected to GPC, which indicated a peak at around 580 to 600 (molecular weight) (Mw/Mn=1.12). From this result, the compound was confirmed to be a dimer of 2,5-bis[(3-ethyloxetan-3-yl)methoxy]norbornane.

The compound was measured for inorganic chlorine content by the method for determination of saponifiable chlorine, described in ISO 4583 and the method described in ISO 4573. The result was that the organic chlorine content was 300 ppm, the inorganic chlorine content was 25 ppm and the total chlorine content was 325 ppm.

Example 13

Synthesis of 1,3-bis(glycidyloxy)adamantane 400 ml of dimethylformamide containing 70 g (0.42 mol) of 1,3-adamantanediol and 30 g (1.25 mols) of sodium hydride was stirred in a nitrogen atmosphere at 70° C. for 2 hours. The resulting mixture was cooled to room temperature. Thereto was dropwise added 151 g (1.25 mols) of allyl bromide in 4 hours, followed by stirring at room temperature for 12 hours. 200 ml of water was added and extraction was made using 500 ml of methylene chloride. The organic layer was washed with water and then subjected to distillation for removal of methylene chloride. Distillation was conducted under reduced pressure for solvent removal, and it was continued to obtain 69 g (0.28 mol, purity: 67%) of 1,3-bis(allyloxy)adamantane.

This was dissolved in 400 ml of methylene chloride. Thereto was added 111 g (0.64 mol) of m-perchlorobenzoic acid, followed by stirring at room temperature overnight. An aqueous sodium sulfite solution was added for decomposition of excessive peracid. The separated m-chlorobenzoic acid was removed by filtration. The organic layer was washed with an aqueous sodium hydroxide solution and water in this order. Methylene chloride was removed by distillation, after which distillation under reduced pressure was conducted to obtain 35 g (0.125 mol, yield: 45%) of 1,3-bis(glycidyloxy)adamantane.

This compound was subjected to MASS spectrometry, $^1$H-NMR spectrometry and elemental analysis. As a result, the compound was confirmed to be intended 1,3-bis(glycidyloxy)adamantane. The results of analyses are shown below.

MASS (EI): molecular weight 280 (M$^+$)
$^1$H-NMR: 1.47 (s. 2H), 1.65 (s. 8H), 1.73 (s. 2H), 2.30 (s. 2H), 2.57 (dd 2H), 2.76 (dd. 2H), 3.06 (m. 2H), 3.41 (dd. 2H), 3.58 (dd. 2H)

The compound was measured for inorganic chlorine content by the method for determination of saponifiable chlorine, described in ISO 4583 and the method described in ISO 4573. The result was that the organic chlorine content was 130 ppm, the inorganic chlorine content was 13 ppm and the total chlorine content was 143 ppm.

Example 14

Synthesis of 5,7-difluoro-1,3-bis(glycidyloxy)adamantane

Using 5 g (24 mmol) of 5,7-difluoro-1,3-adamantanediol, 1.8 g (75 mmol) of sodium hydride, 25 ml of dimethylformamide and 9 g (75 mmol) of allyl bromide, a reaction was conducted in a nitrogen atmosphere in the same manner as in Example 13, to obtain 5.1 g (18 mmol) of 5,7-difluoro-1,3-bis(allyloxy)adamantane.

This was dissolved in 50 ml of methylene chloride. Thereto was added 7 g (41 mmol) of m-perchlorobenzoic acid, and a reaction was conducted in the same manner as in Example 13.

The reaction product was purified by silica gel column chromatography to obtain 4.7 g (15 mmol, yield: 63%) of 5,7-difluoro-1,3-bis(glycidyloxy)adamantane.

MASS (EI): molecular weight 316 (M$^+$)
$^1$H-NMR: 1.0-2.5 (m. 12H), 2.5-4.1 (m. 10H)

Example 15

Synthesis of 5-butyl-1,3-bis(glycidyloxy)adamantane

Using 5 g (22 mmol) of 5-butyl-1,3-adamantanediol, 1.5 g (62 mmol) of sodium hydride, 25 ml of dimethylformamide and 7 g (58 mmol) of allyl bromide, a reaction was conducted in a nitrogen atmosphere in the same manner as in Example 13, to obtain 5.3 g (17 mmol) of 5-butyl-1,3-bis(allyloxy)adamantane.

This was dissolved in 50 ml of methylene chloride. Thereto was added 7 g (41 mmol) of m-chloroperbenzoic acid, and a reaction was conducted in the same manner as in Example 13.

The reaction product was purified by silica gel column chromatography to obtain 4.7 g (14 mmol, yield: 64%) of 5-butyl-1,3-bis(glycidyloxy)adamantane.

MASS (EI): molecular weight 336 (M$^+$)
$^1$H-NMR: 0.7-2.5 (m. 22H), 2.5-4.1 (m. 10H)

Next, the curable polycyclic compounds obtained in the present Examples and Comparative Examples were cured, and the cured materials were measured for the following properties according to the following evaluation methods.

(1) Light Resistance

A light containing a ultraviolet light was applied to a test piece (initial stage: almost colorless and transparent) for 500 hours, using a xenon weatherometer (X 25, a product of Sugai Shikenki). After the light application, the discoloration of the test piece was examined visually and rated in two levels.

(A) Slight yellowing
(B) Severe yellowing (2) Heat Resistance

A test piece (initial stage: almost colorless and transparent) was allowed to stand in an oven of 150° C. for 100 hours. Thereafter, the discoloration of the test piece was examined visually and rated in two levels.

(A) Slight yellowing
(B) Severe yellowing

Example 16

36 g (0.1 mol) of the 1,3-bis[(3-ethyloxetan-3-yl)methoxy]adamantane and 16 g (95 mmol) of 3-methylhexahydrophthalic anhydride as a curing agent were mixed and stirred until they became uniform. Thereto was added 0.16 g of tetrabutylphosphonium diethylphosphorodithioate as a curing catalyst, followed by mixing. The mixture was poured into between two glass plates and cured at 120° C. for 3 hours. The gap between the two glass plates was 5 mm. An almost transparent flat plate (test piece 1) of 5 mm in thickness was obtained.

This test piece 1 was evaluated for light resistance and heat resistance according to the above test methods. The results are shown in Table 1.

Examples 17 to 31

Test pieces 2 to 15 were produced in the same manner as in Example 16, using the curable polycyclic compounds obtained in Examples 2 to 15. These test pieces 2 to 15 were evaluated for light resistance and heat resistance according to the above test methods. The results are shown in Table 1.

Example 31

A test piece 16 was produced in the same manner as in Example 16 except that there were used, as a curable polycyclic compound, the 2,5-bis(glycidyloxy)norbornane obtained in Example 6, in the same amount (mol) as in Example 16 and, as a curing agent, hexahydrophthalic anhydride. The evaluation results therefor are shown in Table 1.

Example 32

A test piece 17 was produced in the same manner as in Example 16 except that there was used, as a curing catalyst, 0.15 g of triphenylsulfonium hexafluorophosphate. The evaluation results therefor are shown in Table 1.

Example 33

A test piece 18 was produced in the same manner as in Example 16 except that there were used, as a curable polycyclic compound, the dimer of 1,3-bis[(3-ethyloxetan-3-yl)methoxy]adamantane obtained in Example 11, in the same amount (mol) as in Example 16 and, as a curing agent, 16 g of 3-methylhexahydrophthalic anhydride. The evaluation results therefor are shown in Table 1.

Example 34

A test piece 19 was produced in the same manner as in Example 16 except that there were used, as a curable polycyclic compound, the dimer of 2,5-bis[(3-ethyloxetan-3-yl)methoxy]norbornane obtained in Example 12, in the same amount (mol) as in Example 16 and, as a curing agent, 16 g of 3-methylhexahydrophthalic anhydride. The evaluation results therefor are shown in Table 1.

Comparative Example 1

An almost transparent flat plate (test piece 20) of 5 mm in thickness was obtained in the same manner as in Example 16 except that there was used, as a curable compound, 34 g of bisphenol A glycidyl ether. The results therefor are shown in Table 1.

Comparative Example 2

An almost transparent flat plate (test piece 21) of 5 mm in thickness was obtained in the same manner as in Example 16 except that there was used, as a curable compound, 35.2 g of hydrogenated bisphenol A glycidyl ether. The results therefor are shown in Table 1.

TABLE 1

|  | No. of test piece | Light resistance | Heat resistance |
| --- | --- | --- | --- |
| Example 16 | 1 | A | A |
| Example 17 | 2 | A | A |
| Example 18 | 3 | A | A |
| Example 19 | 4 | A | A |
| Example 20 | 5 | A | A |
| Example 21 | 6 | A | A |
| Example 22 | 7 | A | A |
| Example 23 | 8 | A | A |
| Example 24 | 9 | A | A |
| Example 25 | 10 | A | A |
| Example 26 | 11 | A | A |
| Example 27 | 12 | A | A |
| Example 28 | 13 | A | A |
| Example 29 | 14 | A | A |
| Example 30 | 15 | A | A |
| Example 31 | 16 | A | A |
| Example 32 | 17 | A | A |
| Example 33 | 18 | A | A |
| Example 34 | 19 | A | A |

TABLE 1-continued

|  | No. of test piece | Light resistance | Heat resistance |
| --- | --- | --- | --- |
| Comparative Example 1 | 23 | B | A |
| Comparative Example 2 | 24 | A | B |

Example 35

Synthesis of 1,3-bis(glycidyloxy)adamantane

In a 200-ml three-necked flask were placed 5.04 g (0.03 mol) of 1,3-adamantanediol and 25 ml of N,N-dimethylformamide. 3.6 g (0.09 mol) of sodium hydride (60% by mass)/liquid paraffin was washed with hexane 5 times and was added to the flask contents with stirring under water cooling. The mixture was heated to 70° C. and stirred for 3 hours. Then, the flask contents were cooled to 5° C. Thereto was dropwise added 10.9 g (0.09 mol) of allyl bromide slowly. After the dropwise addition, the mixture was stirred at 5° C. for 2 hours. Thereafter, 10 ml of water was added to complete a reaction.

To the reaction mixture was added 100 ml of tetrahydrofuran to conduct extraction. The organic layer was washed with water 3 times. The organic layer was subjected to distillation under reduced pressure using a rotary evaporator to remove tetrahydrofuran and N,N-dimethylformamide as much as possible. The resulting liquid was subjected to distillation at 0.1 mmHg at 105° C., to obtain a colorless transparent liquid.

The liquid was subjected to MASS spectrometry, $^1$H-NMR spectrometry and elementary analysis. As a result, the compound was confirmed to be 1,3-bis(2-propenyloxy)adamantane. The results of analyses are shown below.

MASS (EI): molecular weight 248 (M$^+$)

$^1$H-NMR (TMS standard): δ 1.1-2.0 (m, 14H), 4.0-4.3 (m, 4H), 5.2-5.9 (m, 6H)

Elemental analysis: as $C_{16}H_{24}O_2$ Calculated: C, 77.38, H 9.74. Measured: C, 77.76, H 9.63.

The obtained 1,3-bis(2-propenyloxy)adamantane {5.96 g, yield: 80.1%, purity by gas chromatography: 96.0%, purity by gel permeation chromatography (hereinafter referred to as GPC): 99.5%} was dissolved in 30 ml of dichloromethane. Thereto was added 14.3 g (0.058 mol) of 70% m-chloroperbenzoic acid, followed by stirring at room temperature for 16 hours. Then, the reaction mixture was washed with 30 ml of a 25% aqueous sodium sulfite solution and further with water twice. The reaction mixture was subjected to distillation to remove dichloromethane, whereby was obtained crude 1,3-bis(glycidyloxy)adamantane {6.70 g, yield: 79.8% (from adamantanediol), purity by gas chromatography: 96.1%, GPC purity: 99.7%, colorless liquid}. The liquid was subjected to distillation at 0.1 mmHg at 140° C. to obtain, as a colorless transparent liquid, 1,3-bis(glycidyloxy)adamantane {5.36 g, yield: 63.8% (from adamantanediol), purity by gas chromatography: 98.3%, GPC purity: 99.8%}.

Example 36

An operation was conducted in the same manner as in Example 35 except that the allyl bromide used in Example 35 was replaced by 6.89 g (0.09 mol) of allyl chloride and, after the dropwise addition of allyl chloride, stirring was conducted at 5° C. for 5 hours. As a result, after purification by distillation, there was obtained, as a colorless transparent liquid, 1,3-bis(2-propenyloxy)adamantane {5.36 g, yield: 72.0%, purity by gas chromatography: 95.9%, GPC purity: 99.4%}. The amount of crude 1,3-bis(glycidyloxy)adamantane before purification by distillation was 5.99 g {yield: 71.3% (based on adamantanediol), purity by gas chromatography: 96.1%, GPC purity: 99.4%, colorless liquid}. The amount of colorless transparent liquid 1,3-bis(glycidyloxy)adamantane after purification by distillation was 4.67 g {yield: 55.6% (based on adamantanediol), purity by gas chromatography: 98.5%, GPC purity: 99.8%}.

Example 37

An operation was conducted in the same manner as in Example 35 except that the 70% m-chloroperbenzoic acid used in Example 35 was replaced by 76.1 g (0.09 mol) of 9% peracetic acid and stirring was conducted at room temperature for 20 hours.

As a result, after purification by distillation, there was obtained, as a colorless transparent liquid, 1,3-bis(2-propenyloxy)adamantane {6.03 g, yield: 81.0%, purity by gas chromatography: 95.7%, GPC purity: 99.5%}. The amount of crude 1,3-bis(glycidyloxy)adamantane before purification by distillation was 6.04 g {yield: 71.9% (from adamantanediol), purity by gas chromatography: 96.5%, GPC purity: 99.4%, colorless liquid}. The amount of colorless transparent liquid 1,3-bis(glycidyloxy)adamantane after purification by distillation was 4.84 g {yield: 57.5% (from adamantanediol), purity by gas chromatography: 98.6%, GPC purity: 99.7%}.

Example 38

Synthesis of 2,5-bis(glycidyloxy)norbornane

An operation was conducted in the same manner as in Example 35 except that the 1,3-adamantanediol used in Example 35 was replaced by 3.84 g (0.03 mol) of 2,5-norbrnanediol. The compound after purification was subjected to MASS spectrometry, $^1$H-NMR spectrometry and elemental analysis. As a result, the compound was confirmed to be 2,5-bis(2-propenyloxy)norbornane. The results of analyses are shown below.

MASS (EI): molecular weight 208 (M$^+$)
$^1$H-NMR (TMS standard): δ 1.1-2.0 (m, 10H), 4.0-4.3 (m, 4H), 5.2-5.9 (m, 6H)
Elemental analysis: as $C_{13}H_{20}O_2$ Calculated: C, 74.96, H, 9.68. Measured: C, 74.81, H, 9.62.

The obtained 2,5-bis(2-propenyloxy)norbornane (5.06 g, yield: 81.1%, purity by gas chromatography: 96.1%, GPC purity: 99.4%) was subjected to the same operation as in Example 35, for oxidation. As a result, the amount of crude 2,5-bis(glycidyloxy)norbornane before purification was 5.74 g {yield: 79.7% (based on norbornanediol), purity by gas chromatography: 96.2%, GPC purity: 99.6%}. The amount of 2,5-bis(glycidyloxy)norbornane after purification was 4.69 g {yield: 65.1% (based on norbornanediol), purity by gas chromatography: 98.2%, GPC purity: 99.7%}.

Example 39

Synthesis of 1,3,5-tris(glycidyloxy)adamantane

An operation was conducted in the same manner as in Example 35 except that the 1,3-adamantanediol used in Example 35 was replaced by 5.52 g (0.03 mol) of 1,3,5-adamantanetriol. The compound after purification was subjected to MASS spectrometry, $^1$H-NMR spectrometry and elemental analysis. As a result, the compound was confirmed to be 1,3,5-tris(2-propenyloxy)adamantane.

The results of analyses are shown below.
MASS (EI): molecular weight 304 (M$^+$)
$^1$H-NMR: δ 1.1-2.0 (m, 13H), 4.0-4.3 (m, 6H), 5.2-5.9 (m, 9H)
Elemental analysis: as $C_{19}H_{28}O_3$ Calculated: C, 74.96, H, 9.27. Measured: C, 74.56, H, 9.54.

The obtained 1,3,5-tris(2-propenyloxy)adamantane (6.39 g, yield: 70.1%, purity by gas chromatography: 96.2%, GPC purity: 99.5%) was subjected to the same operation as in Example 35, for oxidation. As a result, the amount of crude 1,3,5-tris(glycidyloxy)adamantane before purification was 7.09 g {yield: 67.2% (from adamantanetriol), purity by gas chromatography: 96.5%, GPC purity: 99.5%}. The amount of 1,3,5-tris(glycidyloxy)adamantane after purification was 5.29 g {yield: 50.1% (from adamantanetriol), purity by gas chromatography: 98.5%, GPC purity: 99.8%}.

Example 40

Synthesis of 2,3,5-tris(glycidyloxy)norbornane

An operation was conducted in the same manner as in Example 35 except that the 1,3-adamantanediol used in Example 35 was replaced by 4.32 g (0.03 mol) of 2,3,5-norbrnanetriol. The compound after purification was subjected to MASS spectrometry, $^1$H-NMR spectrometry and elemental analysis. As a result, the compound was confirmed to be 2,3,5-tris(glycidyloxy)norbornane. The results of analyses are shown below.

MASS (EI): molecular weight 264 (M$^+$)
$^1$H-NMR: δ 1.1-2.0 (m, 9H), 4.0-4.3 (m, 6H), 5.2-5.9 (m, 9H)
Elemental analysis: as $C_{16}H_{24}O_3$ Calculated: C, 72.69, H, 9.15. Measured: C, 72.50, H, 9.39.

The obtained 2,3,5-tris(2-propenyloxy)norbornane (5.33 g, yield: 67.3%, purity by gas chromatography: 96.4%, GPC purity: 99.5%) was subjected to the same operation as in Example 35, for oxidation. As a result, the amount of crude 2,3,5-tris(glycidyloxy)norbornane before purification was 5.63 g {yield: 60.2% (based on norbornanetriol), purity by gas chromatography: 96.5%, GPC purity: 99.6%}. The amount of 2,3,5-tris(glycidyloxy)norbornane after purification was 4.35 g {yield: 46.5% (based on norbornanetriol), purity by gas chromatography: 98.5%, GPC purity: 99.7%}.

Comparative Example 3

In a 200-ml three-necked flask were placed 5.04 g (0.03 mol) of 1,3-adamantanediol, 0.2 ml of anhydrous tin tetrachloride and 30 ml of carbon tetrachloride. The mixture was stirred at 5° C. Thereto was dropwise added 6.64 g of epichlorohydrin. After the dropwise addition, stirring was conducted under refluxing for 5 hours. The reaction mixture was allowed to cool and then 40 ml of a 5% aqueous sodium hydroxide solution was added to complete a reaction. The reaction mixture was washed with water 3 times, after which the solvent was removed by distillation to obtain 16.2 g of a yellow viscous liquid. This yellow viscous liquid was dissolved in 20 ml of 2-propanol. Thereto was dropwise added an aqueous sodium hydroxide solution (3 g of sodium hydroxide dissolved in 3 g of water) at room temperature, followed by stirring for 3 hours. Then, 50 ml of water and 50 ml of ethyl acetate were added to conduct extraction. The organic layer was washed with water 2 times, and the solvent was removed by distillation to obtain 10.8 g of a yellow liquid. This crude 1,3-bis(glycidyloxy)adamantane had a gas chromatography purity of 54.4% and a GPC purity of 30.2% and contained a large amount of a high-molecular compound.

The crude product was subjected to distillation under reduced pressure (0.1 mmHg, oil bath temperature: 175° C.). However, 1,3-bis(glycidyloxy)adamantane was unobtainable and the flask contents cured and became gel-like.

The invention claimed is:

1. A curable polycyclic compound represented by the following formula (4):

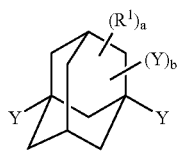

(4)

wherein $R^1$ is an alkyl group of 1 to 4 carbon atoms, a perfluoroalkyl group of 1 to 4 carbon atoms, or a fluorine atom; a is an integer of 0 to 2; b is an integer of 0 to 2; and Y is a group represented by the following formula (3.1):

(3.1)

2. A curable polycyclic compound according to claim 1, wherein, in the formula (4), a is 0 (zero).

3. A curable polycyclic compound according to claim 1, wherein the content of the halogen molecule or halogen ion contained as an impurity is 100 to 2,000 ppm.

4. A curable polycyclic compound represented by the general formula (7.1):

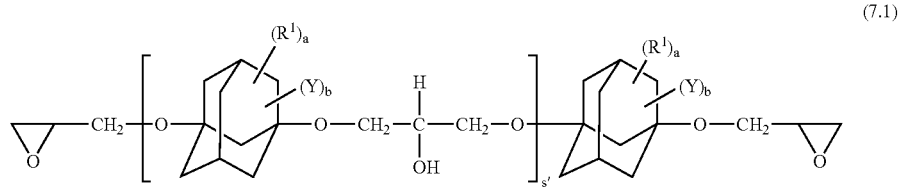

(7.1)

{wherein $R^1$, Y, a and b have the same definitions as in the formula (4); and s' is an integer of 1 to 3}.

5. A curable composition characterized by comprising a curable polycyclic compound set forth in claim 1 and a curing agent.

6. An encapsulant for light-emitting diode, comprising a curable composition set forth in claim 5.

7. A light-emitting diode encapsulated by an encapsulant set forth in claim 6.

* * * * *